(12) United States Patent
Chambon et al.

(10) Patent No.: US 6,444,438 B1
(45) Date of Patent: Sep. 3, 2002

(54) METHOD FOR THE PREPARATION OF A PROTEIN BY YEASTS USING AN INDUCIBLE SYSTEM, VECTORS AND CORRESPONDENCE TRANSFORMED STRAINS

(75) Inventors: Pierre H. Chambon, Blaesheim; Daniel Metzger, Illkirch-Graffenstaden; John White, Strasbourg, all of (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 08/453,998

(22) Filed: May 30, 1995

Related U.S. Application Data

(63) Continuation of application No. 08/161,064, filed on Dec. 3, 1993, now abandoned, which is a continuation of application No. 08/044,079, filed on Apr. 6, 1993, now abandoned, which is a continuation of application No. 07/798,993, filed on Dec. 2, 1991, now abandoned, which is a continuation of application No. 07/373,524, filed on Jun. 30, 1989, now abandoned.

(30) Foreign Application Priority Data

Jul. 1, 1988 (FR) .............................................. 88 08978

(51) Int. Cl.$^7$ ......................... C12P 21/56; C12N 15/81; C12N 15/63
(52) U.S. Cl. ................... 435/69.1; 435/320.1; 435/254; 435/255; 435/285; 536/23.1; 536/23.5; 536/24.1; 536/24.2
(58) Field of Search ............................. 435/69.1, 320.1, 435/172.3, 254, 255, 285; 536/23.1, 23.5, 24.1, 24.2; 935/34, 43, 69, 6, 7, 8, 9, 37

(56) References Cited

U.S. PATENT DOCUMENTS 5,071,773 A * 12/1991 Evans et al. ................ 436/501
5,175,105 A * 12/1992 Meyhack et al. ........... 435/215

FOREIGN PATENT DOCUMENTS

EP 0258067 * 2/1988

OTHER PUBLICATIONS

Martinez et al. 1987. Embo J. 6, 3719–3727.*
Strathern et al. 1981. in: The Molecular Biology of the Yeast Saccharomyces–Life Cycle and Inheritance. Cold Spring Hrbor Laboratory. Cold Spring Harbor, NY. p. 99.*
Green et al. 1986 Nature 320, 134–139.*
West et al. 1984 Molec. Cell. Biol. 4, 2467–2478.*
Jost et al. 1984 Proc. Natl. Acad. Sci. USA. 81, 429–433.*
Feldman et al. 1984. Proc. Natl. Acad Sci. USA. 81, 4722–4726.*
Feldman et al. 1984 Science. 224, 1109–1111.*
Burshell et al. 1984. J. Biol. Chem. 259, 3430–3456.*
Feldman et al. 1982 Science 218, 297–299.*
Cushing et al. 1986. Trans. Ill. Acad. Sci. 79, 111–116.*
Green et al. 1988 Nuc. Acids. Res. 16, 369.*
Knist et al. 1986, Embo J. 5, 891–897.*
Ma et al; Cell, vol. 51, Oct. 9, 1987; pp. 113–119.
T. Etcheverry et al; Biotechnology, vol. 4, No. 8; (Aug., 1986) pp. 726–730.
Metzger et al; Nature, vol. 334, Jul. 7, 1988, pp. 31–36.
Webster et al; Cell, vol. 52, Jan. 29, 1988, pp. 169–178.
Kakidani et al; Cell, vol. 52, Jan. 29, 1988, pp. 161–167.
French Search Report—FR 8808978 FA 413113.
The Journal Of Biological Chemistry, vol. 267, No. 16, Issue of Jun. 5, pp. 11191–11195, 1992, entitled Glucocorticoid-specific Gene Activation by the Intact Human . . . Yeast, by Wright, et al.
Proc. Natl. Acad. Sci. USA, vol. 90, pp. 4281–4285, May 1993, entitled "Efficient transactivation by retinoic acid receptors in yeast requires retinoid X receptors", by Heery, et al.
Molecular Biology of the Gene, General Principles, vol. 1, Fourth Edition, Watson et al., 1987, pp. 274–277 and 738–739.

* cited by examiner

*Primary Examiner*—Christopher S. F. Low
(74) *Attorney, Agent, or Firm*—Fitch, Even, Tabin & Flannery

(57) ABSTRACT

The present invention relates to a method for the preparation of a protein by yeasts. In particular, the method of the invention concerns transforming a yeast cell with a first DNA fragment encoding the protein and a second DNA fragment that encodes the receptor. The method further entails culturing the transformed yeast cell, and isolating the protein. The first DNA fragment is under control of elements providing for expression of the DNA fragment in yeast, which elements include a higher eukaryotic positive transcription control sequence consisting of a natural ligand responsive element activating sequence or a variant. The receptor is a natural nuclear receptor selected from the group consisting of receptors for steroids or for retinoids or for thyroid hormones or for vitamin D3. The receptor includes a first fragment that recognizes said ligand and a second fragment that binds to said transcriptional control sequence.

10 Claims, 10 Drawing Sheets

ERE
5'-GATCCAATATTCCTGGTCAGCGTGACCGGAGCTGA-3'
3'-GTTATAAGGACCAGTCGCACTGGCCTCGACTCTAG-5'

EREM
5'-GATCCAATATTCCCCGTCAGCGTGACCGGAGCTGA-3'
3'-GTTATAAGGGGCAGTCGCACTGGCCTCGACTCTAG-5'

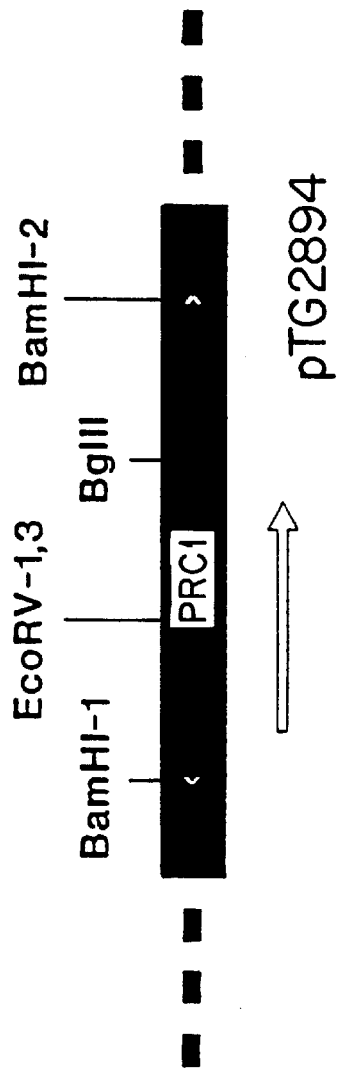
FIG. 5a
FIG. 5b

METHOD FOR THE PREPARATION OF A PROTEIN BY YEASTS USING AN INDUCIBLE SYSTEM, VECTORS AND CORRESPONDENCE TRANSFORMED STRAINS

This is a continuation of application Ser. No. 08/161,064, filed on Dec. 3, 1993, which was abandoned upon the filing hereof which is a cont. of Ser. No. 08/044,079 filed Apr. 6, 1993 now abandoned, which is a cont. of Ser. No. 07/798, 993 filed Dec. 2, 1991 now abandoned, which is a cont. of Ser. No. 07/373,524 filed Jun. 30, 1989 now abandoned.

The invention relates to inducible expression systems, to the corresponding transformed strains and to methods for obtaining them for producing proteins, in particular heterologous proteins, in yeasts.

The recombinant DNA technique enables genes for heterologous proteins to be expressed in yeasts. Thus, the construction of vectors containing yeast promoter sequences corresponding to the genes for glycolytic enzymes of *Saccharomyces cerevisiae*, such as 3-phosphoglycerate kinase (PGK), an alcohol dehydrogenase (ADH1) or glyceraldehyde-3-phosphate dehydrogenase (GPD), has enabled important proteins to be produced by fusion of their coding sequence to the yeast promoter, for example leukocyte interferon according to Hitzeman R. A. et al., Nature 293, 717–722 (1981) or hepatitis B surface antigen according to Bitter G. A. et al., Gene 263–274 (1984).

In many cases, it has been observed that the heterologous protein produced is toxic for the host cell, and leads to instability of the plasmids and the selection of cells which no longer express the protein in question. Methods enabling the expression of the gene for the protein to be repressed during the cellular growth phase, and then a high production of the protein to be induced during the final stage of culture, have been found using a promoter regulated by a change in carbon sources, for example the promoter of the galactokinase gene (GAL1) or the promoter of the uridinediphosphoglucose 4-epimerase gene (GAL10) which correspond to two of the four genes responsible for the utilization of galactose in yeast and whose expression is repressed by glucose and induced by galactose. Vectors comprising the GAL1 promoter linked to a heterologous gene have been described, enabling yeast to be grown in a medium containing glucose, and the protein then to be expressed when galactose is present in the medium. Yeast strains transformed with such vectors are described, for example, in British Patent Application 2,137,208, and these vectors, under the control of the GAL1 promoter, express in the presence of galactose proteins such as bovine growth hormone or prorenin. Most yeast promoters contain, upstream from TATA elements which mediate transcription initiation, elements which regulate transcription, "upstream activator sequences" (designated UAS), which represent the binding site of proteins which regulate transcription, such as GAL4 for the activation of the genes of galactose metabolism, these proteins themselves being under the control of their own promoters.

Different means have already been proposed for improving the efficiency of transcription of heterologous genes in yeasts. In particular, it has been proposed to use hybrid promoters which contain, upstream from the TATA element of a constitutive yeast promoter, an extrinsic UAS regulatory sequence, such as UASg which corresponds to the GAL1–GAL10 intergenic sequence and which is inserted, for example, upstream from the TATA element of a constitutive yeast promoter, such as GPD as described in Patent Application WO 86/00,680, or such as PGK as described in European Patent Application 258,067. The inserted UASg sequences enable the constitutive promoter to be successively repressed and then expressed by the carbon source used, such as glucose as a repressor and galactose as an inducer.

However, the use of promoters in general or of any hybrid promoter involves a control over totally repressed or induced levels, which is difficult to achieve because these levels involve a group of proteins which regulate transcription. Thus, the GAL4 gene activates transcription by the presence of galactose, which is directly or indirectly responsible for the dissociation of a complex between GAL4 and an antagonistic protein GAL80, while other proteins appear to be involved in the repression by glucose, such as GAL82 and GAL83 according to Yocum R.R. et al., MBC 4 1985–1998 (1984).

In addition to the drawbacks mentioned above, this type of system based on induction with galactose and/or repression with glucose is not very versatile; in effect, it cannot be used for yeasts which do not assimilate glucose and/or galactose and cannot be used in the case where one of these components constitute all or part of the carbon substrate of the culture medium.

It is hence advantageous to have available in yeasts inducing systems capable of being induced by products which are not in themselves necessary for the culturing of these cells, which is the case, for example, with hormones, in particular steroid hormones.

Thus, the present invention relates to a method for the preparation of a protein by yeasts, according to which:
yeast cells which contain the following are cultured:
  a DNA sequence coding for the said protein under the control of elements providing for its expression in yeasts, the said elements comprising a transcription control sequence which is inducible by a complex formed by a receptor and a ligand,
  a DNA sequence which is functional in yeast, coding for the said receptor, the receptor comprising two essential portions, one of which recognizes the ligand so as to form a complex with the said ligand and the other binds to the said transcription control sequence; the portion of the receptor which recognizes the ligand is preferably of higher eukaryotic origin, and the ligand is not necessary for the culturing of the cells but is capable of entering the said cells when added to the culture medium,
the said ligand is added to the culture medium at an appropriate time point for induction,
the synthesized protein is recovered.

The expression of proteins by yeasts using recombinant DNA techniques is considered to be well known to those versed in the art. A considerable number of publications have already described the preparation of proteins, in particular heterologous proteins, by means of yeasts, using expression vectors. These expression vectors contain, more often than not, apart from the sequence coding for the said protein, the elements controlling its expression in yeasts, that is to say, in general, a promoter and a terminator.

In most cases, these vectors are nonintegrative vectors, that is to say plasmids; they then contain an origin of replication which is efficacious in yeasts, in particular the origin of the $2\mu$ plasmid or an ars sequence peculiar to the said yeast.

These nonintegrative expression vectors contain, in addition, elements enabling provision to be made for their maintenance in the cells, either using as a selection marker a gene for resistance or alternatively an element complementing an auxotrophy of the host strain, URA3 or LEU2 for example.

In some cases, and in order to overcome the drawbacks linked to the use of self-replicating vectors, it has been possible to develop vectors providing for the integration of the sequences in question at chromosomal level. This type of vector enables a more stable strain to be obtained, but the amplification in respect of expression is sometimes smaller than with a nonintegrative plasmid.

Integration vectors contain, more often than not, at least one sequence homologous with a chromosomal sequence which will provide for exchange and integration.

It must be understood that, since the present invention relates essentially to the induction of transcription, the expression vectors which will be used can be of either the integrative or the nonintegrative type.

Although the method in question is more especially intended for the preparation of heterologous protein, it is possible to use it for expressing yeast proteins, in particular in the case of systems providing for the hyperexpression of a gene which can lead, in some cases to cell death before the optimum biomass is obtained.

"Heterologous protein" is understood to mean a protein foreign to the host cell which expresses it, that is to say different in origin from that of the host cell which, according to the invention, is a yeast. The protein can be of bacterial origin, for example *Escherichia coli* beta-galactosidase, or of higher éukaryotic origin, for example of human origin, such as, for example, lymphokines, blood coagulation factors, hormones, vaccinal antigens and, generally speaking, any protein of therapeutic or industrial interest.

As has been stated, the essential feature of the invention is the combination of a transcription control sequence and a receptor complexed to a ligand. The choice of the first is conditioned by the choice of the second.

Among usable transcription control sequences, there may be mentioned, in particular, the sequences which are usually functional in higher éukaryotic cells, that is to say natural sequences activating the transcription of higher éukaryotic cells, such as, for example, an HRE (for "hormone responsive element") or a variant or synthetic derivative of such a sequence, and which also fulfils in yeast this function of activation of transcription. These sequences are, in general, natural or synthetic, perfect or imperfect palindromic sequences.

Thus, for example, in the case where the transcription control sequence used is an HRE sequence, the receptor is the corresponding hormone.

As stated above, the transcription control sequence represents one of the elements providing for the expression of the desired protein in yeast. Provision for the expression in yeast may hence be made by hybrid sequences which comprise, apart from the transcription control sequence defined in the context of the invention, sequences corresponding to yeast promoter sequences. Among usable promoters, there may be mentioned the inducible promoter GAL1 referred to above, and also constitutive yeast promoters such as the PGK promoter.

In general, the TATA element of the promoter is retained and the transcription control sequence may be placed at variable distances upstream from the TATA element. It is especially advantageous to be able to have available a minimal structure for the hybrid promoter, that is to say a structure in which the distance between the TATA element and the transcription control sequence is small while remaining sufficient to provide for satisfactory inducibility.

"Receptor" in the sense of the invention is hence understood to mean a protein which is functional in higher éukaryotic cells, or variants or corresponding synthetic derivatives which display in yeast the functional properties of the native receptor.

The term "receptor" also comprises chimeric proteins, that is to say a structure in which the two essential portions are of different origins. For example, a preferred combination consists in preparing a hybrid receptor in which the portion which recognizes the ligand is of higher éukaryotic origin and the portion which binds to the transcription control sequence is of yeast origin, but it is possible to use sequences originating from any other microorganism, for example bacteria. The transcription control sequence then comprises a sequence which is functional in yeasts, that is to say a natural sequence activating transcription in yeasts. There may be mentioned, for example, the UAS of the GAL1 promoter, which is a yeast promoter.

The subject of the invention is hence the different functional combinations between a transcription control sequence, whether natural or derived, in particular, by chemical synthesis, and the receptor which can be a natural, derived or chimeric receptor. The nature of the ligand is, in turn, determined by the choice of receptor.

Among usable receptors, there should be mentioned nuclear receptors, in particular for a steroid, and other nuclear receptors, for example for retinoids or for thyroid hormones, as well as vitamin D3. The receptor for a steroid can be a natural receptor for steroid hormones, for example the estrogen receptor, the progesterone receptor or the testosterone receptor, or a variant receptor or chimeric derivative, which is functional with respect to the transcription control sequence. The steroid can be a natural steroid such as estradiol, progesterone or testosterone, or an analog or derivative, which is functional in the complex to which the transcription control sequence contained in the vector of the invention is sensitive.

The estrogen receptor can be the natural receptor (hereinafter designated hER) or a variant or chimeric derivative which is functional in the presence of estradiol with respect to the transcription control sequence contained in the vector of the invention.

More especially, the subject of the invention is the case where the essential portion of the receptor recognizing the ligand originates from the human estrogen receptor designated hERG which, compared with the receptor designated hER, has a glycine instead of a valine at position 400, the ligand then being estradiol. According to a feature of the invention, the whole of the hERG receptor may be used as the receptor.

Compared with the human estrogen receptor hER, the complementary DNA sequence of which had been published in Green S. et al. (1986) (Nature, 320, 134–139), the hERG receptor hence comprises a glycine in place of a valine at position 400. The DNA sequence and deduced amino acid sequence published in Green et al. are as follows:

```
                                                                                                                                                                                                                                                                                                                                                                                                        SmaI(a)
    -128  GAG TGTGCCTGGAGTGATGTTTAAGCCAATGTCAGGGCAAGGCAACAGTCCCTGGCCGTCCTCCAGCCACCT TTGTAATGCATATGAGCTCGGAGACCAGTACTTAAAGTTGGAGGCCC

-8  GGGAGCCCAGGAGCTGGCGGAGGGCGTTCGTCCTGGGAGCTGCACTTGCTCCGTGGGTCGCCGGCTTCACCGGACCGCAGCTCCGGGGGCCGGGGCCCAGAGCTCCGTGTCGG
                                                                                                                           SacII(a)
     113  CGGGACATGCCTGCGTCGCCTTCTAACCTCGGCCGTGTCGCTTTTTCCAGGTGGCCCGCCGCCTTCGCCCTGCGGGGACACGGTCTGACCCTGCCGGCCACCGACC                           30

233  ATG ACC ATG ATG ACC CTC CAC ACC AAA GCA TCT GGG ATG GCC CTA CTG CAT CAG CAG ATC CAA GGG AAC GAG CTG GAG CCC CTG AAC CGT CCG CAG
          Met Thr Met Met Thr Leu His Thr Lys Ala Ser Gly Met Ala Leu Leu His Gln Gln Ile Gln Gly Asn Glu Leu Glu Pro Leu Asn Arg Pro Gln    60
                                                                                                                                           SmaI(c)
     323  CTC AAG ATC CCC CTG GAG CGG CCC CTG GAG TAC CTG GTC CTA TAC CTG CAG AGC AGC AAG CCC GTG TAC AAC TAC CCC GAG GGC GCC TAC            90
          Leu Lys Ile Pro Leu Glu Arg Pro Leu Glu Tyr Leu Val Tyr Leu Gln Ser Ser Lys Pro Val Tyr Asn Tyr Pro Glu Gly Ala Ala Tyr
                                                                                                                       PvuII(b)
     413  GAG TTC AAC GCC GCG GCG GCG AAC CAT CAA GCG CAG GTC TAC CTG GAA AAC GAG CTG GGC CCC TCT GAG GCT GCG GCG TTC GGC                   120
          Glu Phe Asn Ala Ala Ala Ala Asn His Gln Ala Gln Val Tyr Leu Glu Asn Glu Leu Gly Pro Ser Glu Ala Ala Ala Phe Gly

503  TCC AAC GGC CTG GGG GGT TTC CCA CCA GTG TCT CCG AGC AAC CTC ATG CTG TAC AAC GAG GTG CGC CAC CTG CAG CCG CCG CAC TTC CCT          150
          Ser Asn Gly Leu Gly Gly Phe Pro Pro Val Ser Pro Ser Asn Leu Met Leu Tyr Asn Glu Val Arg His Leu Gln Pro Pro His Phe Pro

593  CTG CAG CCC CAC GGC CTG ATG CAG GTG CAG CTC GAG AAC GAG TAC AAC CTG ATG TAC ACG GGC TAC TAC ACC AAT GAC GTG CGC CCG GCA TTC TAC  180
          Leu Gln Pro His Gly Leu Met Gln Val Gln Leu Glu Asn Glu Tyr Asn Leu Met Tyr Thr Gly Tyr Tyr Thr Asn Asp Val Arg Pro Ala Phe Tyr

683  AGG CCA AAT CGA AAT CGC GGT GGC ATG TTG GCC AGA AGA CGA AAA GAC ATG GGA ATG GCT ATG AAG GGA AGT GAG GCC ATG GCC ATG GAA TCT GCC AAG  210
          Arg Pro Asn Arg Asn Arg Gly Gly Met Leu Ala Arg Arg Arg Lys Asp Met Gly Met Ala Met Lys Gly Ser Glu Ala Met Ala Met Glu Ser Ala Lys

773  GAG ACT CGC TAC TGT GCA GAT GCT TCA GGC TAT CAT GAC TGG GTC TGT GAG GGC TGC AAG AAG AGC TGC CAG GCC TGC                          240
          Glu Thr Arg Tyr Cys Ala Val Cys Asn Asp Tyr Ala Ser Gly Tyr His Tyr Gly Val Trp Ser Cys Glu Gly Cys Lys Ala Phe Phe Lys

863  AGA AGT ATT CAA GGA CAT AAC CAG ACC TAT ATG TGT CCA GCC AAA AAC GAC TGT ATT GAT GAC AGA AGA GGA AAT TTG AAA AAG CAC ATG CAG         270
          Arg Ser Ile Gln Gly His Asn Gln Thr Tyr Met Cys Pro Ala Lys Asn Asp Cys Ile Asp Asp Arg Arg Gly Asn Leu Lys Lys His Met Gln

953  CGG CTC CGC AAA TGC TAC GAA GTG ATG GGA GGT GTG GGT GAA GTG CTT TGG CCA AGC CTC ATG ATC TAT TCC GAG                                300
          Arg Leu Arg Lys Cys Tyr Glu Val Met Gly Gly Gly Val Gly Glu Val Leu Trp Pro Ser Leu Met Ile Tyr Ser Glu

1043  AGA GAT GAT GGG GGC GAG GGT GGT GAA GTG TCC CTG ACG GCC CAG CAG GTC GAT GCT GTC AGT GCA GAG GAG CTG GCA AGG AGC CTG TTG AAT CTC    330
          Arg Asp Asp Gly Gly Glu Gly Gly Glu Val Ser Leu Thr Ala Gln Gln Val Asp Ala Val Ser Ala Glu Glu Leu Ala Arg Ser Leu Leu Asn Leu

1133  TCT AAG AAG AGC AGC CTG TCC TTC GAA CCC TCG AGT GCT CTG GAG GAC CTG CTT CAC GTT CAC CTA GAG ATC CTG ATG AAG TGG                   360
          Ser Lys Lys Ser Ser Leu Ser Phe Glu Pro Ser Ser Ala Leu Glu Asp Leu Leu His Val His Leu Glu Ile Leu Met Lys Trp

1223  TAT GAT CCT ACC AGA CCC AGA TTC AGT GAG GCT CGA GTT CAC CTC CAT GAT TTG GTG CAG GAT CCG TTG TGC CTA GAG ATC CTG ATG AAG TGG      390
          Tyr Asp Pro Thr Arg Pro Arg Phe Ser Glu Ala Arg Val His Leu His Asp Leu Val Gln Asp Pro Leu Cys Leu Glu Ile Leu Met Lys Trp

1313  GCG AAG AGG GTG CCA GGC TTT GTG GAT TTG CCA CTG GAT GAC CAG GTC CAC CTC CTA CTA GAG ATC CTG ATG AAG GGT
          Ala Lys Arg Val Pro Gly Phe Val Asp Leu Pro Leu Asp Asp Gln Val His Leu Leu Leu Glu Ile Leu Met Lys Gly
```

```
1403  CTC GTC CGC ATG GAG CAC GTG CCA AAG CTG TTT GCT CTA GAC AGG AAC TTG CTC TTG GAC AGG AAA TGT GTA GAG GGC    420
      Leu Val Arg Met Glu His Val Pro Lys Leu Phe Ala Leu Asp Arg Asn Leu Leu Asp Arg Lys Cys Val Glu Gly

1493  ATG GTG GAG ATC TTC GAC ATG CTG GCT ACA TCA TCT CGG TTC CGC ATG ATG CTG AAT CTG GGA GAG GAG TTT GTG TGC CTC AAA TCT    450
      Met Val Glu Ile Phe Asp Met Leu Ala Thr Ser Ser Arg Phe Arg Met Met Leu Asn Leu Gly Glu Glu Phe Val Cys Leu Lys Ser

1583  ATT ATT TTG CTT AAT TCT GGA GTG TAC TAT TTT CTG TCC AGC ACC CTG AAG GAG AAG GAG CAT CAC CGA GTC CTG GAC    480
      Ile Ile Leu Leu Asn Ser Gly Val Tyr Tyr Phe Leu Ser Ser Thr Leu Lys Glu Lys Glu His His Arg Val Leu Asp

1673  AAG ATC ACA GAC ACT TTG ATC CAC ATG GCC AAG GCA AAA CTG AGT CAC CGG CAG CTG CTG CGG CTG CTC CTC ATC    510
      Lys Ile Thr Asp Thr Leu Ile His Met Ala Lys Ala Lys Leu Ser His Arg Gln Leu Leu Arg Leu Leu Leu Ile

1763  CTC TCC CAC ATC AGG CAC ATG AGT AAA AAG CAC ATG GAG CAT CTG TAC AAG TGC AAC GTG CCC CTC TAT GAC CTG CTG    540
      Leu Ser His Ile Arg His Met Ser Lys Lys His Met Glu His Leu Tyr Lys Cys Asn Val Pro Leu Tyr Asp Leu

1853  CTG GAG ATG CTG GAC GCC CTA CAT GCG GCC CGT AGC ACT GCG GGA TCC GAG GTG GAG ACG GAC AGC CAA GTC GAG CTC ACT    570
      Leu Glu Met Leu Asp Ala Leu His Ala Pro Thr Ser Arg Gly Ala Ser Val Glu Thr Asp Ser Gln Val Glu Leu Thr

1943  GCG GGC TCT ACT TCA CAT TCC TTG CAA AAG TAT TAC ATC ACG GGG GAG GCA GGT TTC CCT GCC ACA GTC TGA GAG CTC CCT GGC    595
      Ala Gly Ser Thr Ser His Ser Leu Gln Lys Tyr Tyr Ile Thr Gly Glu Ala Gly Phe Pro Ala Thr Val ***

2033  TCCCACACGGTTCAGATAATCCTGCTCATTTACCCTCACACTTCTGTCTCCTGCATGCATCCGGCATGATCCAACACACTCTAAATCTTTGTAACACTTTCCCCTTGCCATGTACT
2153  GGCCATTCATTTGCTTGCTAGTGGAGCACTGCACATTCTTGTCTTCTGTTCAGTTCCTCAGTTCTGCATTCTAAGCTGAACTCTCAGATAACTCTGTGCATTGGTTGACTTGTGTGTGG
2273  AAGCGTGAGGATTCCCGTAGCTCTCACAGCTGAATAAGCAAAGAATTTAAAGTGGCTCTCAGATGGCTTGTGGCCTATGGGGACCCTGGATGGGTGCCTCCCCCAGCCCTGTGAAGGGTTTATTATAGCACCCCCTCTGTAT
2393  CTGATAAGCACTCTTTAAATGCTCTAAGAATAAGCCACACCTTAAAGTGCTCTAAAGTGTTTATATGACTGTAGCAGAGTATCTGGTGATTGTCAATTCACTTCCCCTCTGGCTTTCCGGTCATGGGTTCCAGTTAATCATGCCTCCC
2513  TCCTATGGCAATGCATCCTTTATGAAAGTGCCAAGACTTATTTTAACTTGATACTACTTAAAGCTTCAGAATTGTAGCAGAGTATCTGAAGCTCTGCTTTCTGGGTATCCCTAGAATACAAGGCGTAATGTCGGATA
2633  GGAAGGCAGATCCCCTAGTTGGCCAAGACTTATTTAGTTAAGCATGGAAGACTTGTAGACAAGTGCTGTGTCCTCAAGTTGTAATAATCAAAATCAGGGTTGGTTGGGCACCACAGGAAAAATCCTCCGTTCCTGTGCAG
2753  ATGGACCTATGGAGAACAAGAAGTTGATCTTAGTTAAGCTCCTATATGAGGATAAGTTCCTGATTTTTGTTTTTATTTTGTGTAACAAAAGAAAGCCCTCCTCCTGAACTTGCA
2873  GTAAGGTCAGCTTCAGGACCTCTGTTCCAGTGGGCACTGTACTTGGATCTTCCCGGCGTGTGTGCCTTACACAGGGGTGAACTGTTCACTGTGTGATGCATGAGGTAAATGTAG
2993  TTGAAAGGAGCAGGGGCCTCAGAGTGTTGCATTTAGCCCTGGGATGGAGCTTGTGGCTACTACAGAACAAGAGGGAAAGTAGGGCAGAAACTGGATA
3113  CAGTTCTGAGCACAGCAGCCAGAGCTGCTCAGGTGGGCCTGGCACAGGGCTCTGCAGACCCCGACAATTGGCCCCAGCACCCTGGGCGTGGGAGACCGTTGC
3233  GCTCTTATTCATTTCCCAGCGTGACTGGGCGTGGTTGGGAAGAAGCAGCTGTCAAGTTGTAGACAAGTGTTCCTACAATGTCCCAGCACCCTGGGGAAGAAATCAGGGTTTGGTTTGGGAAGAAATCCTCCGTCCA
3353  TGTCACTACTCAGGCTGACTGGGCCTCCAGCTCATTCTGCCCAGCTCATTCCTCTTGGGCCTCATGGGAAGTCAAATTCAGGGTTCATTCAGCCCACACAGGCCAGCCTTCCCTGGCCTTTGCTTCTCTAG
3473  GTTCCCTACGGCCTCCTTTTCTTCTTTAACAAAAAATGTTTGATTTCTTGACTTAGTGCTAATTAAGAAAGGCTCAAAAATACTAAAAAGAAAGGCTCAAAAAAATCCCACCACCACTTATTGAGAGGTCAATAGCCCACCC
3693  CACAATTATGGGTTACTTCCTTTTCTTAACAAAAGAATGTTTGATTTCTTCAATTTGTTTGTGTAATTGAAAAAGTGGAATTTCATTCATTCTCCAGTTAAGTAATGTCCAAAAGGACTGAGAATCGGCAAAAAAAAA
3713  AGGTAGCTGCTCGGGCTTTCTCATTGGTATGTCTTGTTGTTGAAAAGTGGAATTCATTCATTCTCCAGTTAAGTGATGTCCAGTTAAGTGATGTCCAAAAGGACTGAGAATCGGCAAAAAAAAA
3833  AAAAAGTTTTATGTGCACTAAATTTGCGACAATTTATGTATCTGTTAAGAACATAATCTTTGTGCTTGTTGTTTAAGAAGCACCTTAGTTTGTTTAAGA
```

-continued

| | |
|---|---|
| 3953 | AGCACCTTATATAGTATAATATATATTTTTTGAAATTACATTGCTTGTTTATCAGACAATTGAAATGTAGTAATTCTGTTCTGGATTTAATTGACTGGGTAAACATGCAAAAACCAAGG |
| 4073 | AAAAATATTAGTTTTTTTTTTTTTTTGTATACTTTTCAAGCTACCTTGTCATGTGATATACAGTCATTTATGCCTGTGATTATTCATTAAATGAAGATCACATTTCATCTC |
| 4193 | AACTTTTGTATCCACAGTAGACAAAATAGCACTAATCCAGATGCCTATTGTTGGATATTGAATGACAGACAATCTATGTAGCAAAGATTATGCCTGAAAGGAAAATTATTCAGGGCAG |
| 4313 | CTAATTTTGCTTTTACCAAAAATATCAGTAGTAATATATTTTGACACAGTAGCTAATGTTTATACTTAGATTTCTTTAAAAAAATTAAAATAAAACAAA |
| 4433 | AAAAATTTCTAGGACTAGACGATGATTGAAGGCTAAAGCCAAAACAATTATACAGTGGAAGTTTTACATTATTCATCCAATGTGTTTCTATTCATGTTAAGATACTACTACATTTGAAG |
| 4553 | TGGGCAGAGAACATCAGATGATTGAAATGTTCGCCCCAGGGGTCTCCAGGAAATCTCTTTGCCTCTGCTTTCCCCCACTCTGAGGGAAGTTAAAATGTTGAATTATCTGGGGGGCTCAGGTATGGTGGGGA |
| 4673 | AGTGGATTCAGGAATCTGTAGGAACATGATTTAAAAAAAAAATCTTTAAGAAGATATTGAGAGAAAACTCTTTGAAAGTATTTGGAGGAAAAATGTTAATTCTGGGTGTGCACCAAGGTTGATTTATCTGGGGCTCAGTAGAGTCCACTTCTGCCCTGGA |
| 4793 | GACCACAAATCAACTAGCTCCATTTACCAGCCATTCTAAATGCCATTCTATAATGCCAAGCCAATATGTTTAACCAAGCCATAGCCTTGAGAATAGCTAGTGCTCTGCAAAATCTAACCCCTAAGGAA |
| 4913 | CGCCATTGCCTGCAGCTTGCCGTAATGATTCATTTGATTTGAATTCCCTAGTAACCTTGCAGATATGTTTAACCAAGCCATAGGCCATGCCACTGTTACACACTGAAATTGGTTAAACCAAGCCATTGATTAGAAATAACTTTCTATACTTTCC |
| 5033 | GTGCAGTCTTTGATTTGATTTCCCTAGTAACCTTGCAGATATGTTTAACCAAGCCATAGGCCATGCCACTGTTACACACTGAAATTGATTTAACCAAGCCATAGGCCATGCCACTGTTACACACTGAAATTGGTTAAACCAAGCCATTGATTAGAAATAACTTTCTATACTTTCC |
| 5153 | TAAGGTGTTCTCACCTTGAAATCTTATACACTGGGAGTGATCACTAACACCATAGTAATGCTCAACTCAGGTCTAGATTACACTGCATTTCTTCCAAGTTAATCCCCTGAAAACTTACTCTCAACTGGAGCAAATGAACTT |
| 5273 | AATTATGAGATGGACTGTGGGTACTGGGAGTGATCACTAACACCATAGTAATGCTCAACTCAGGTCTAGATTACACTGCATTTCTTCCAAGTTAATCCCCTGAAAACTTACTCTCAACTGGAGCAAATGAACTT |
| 5393 | AGCTCAAAAGGCAACCATAATTCTCTTTGGTCAAGTAGCGTTAATTATGCTCGTTCCAACTGCATTTCTTTGCAGAGCTCGTTAATTATGCTCGTTCCAACTGCATTTCTTCCAATTGAATTAAAGTGTGGCCTCGTTTTAGTCATTTAAAATTGTTTCTAAGTA |
| 5513 | TGGTCCCAAATATCCATCTTTTCAGTAGCGTTAATTATGCTCGTTCCAACTGCATTTCTGTTTCCAACTGCATTCAATTGATTTTTTTGCATCCAATTGTGCCTGACACAGACCCCTTTGCATTCACAGAGAGTCATTGGTT |
| 5633 | ATTGCTGCCTCTATTATGGCACTTCCAATTTCAGTGTGTGTTTAGAGCTGTGTGCACCCTAGAAACAACTACTTGTCCCATCAGCAGGTGCCTGACACAGACCCCTTTGCATTCACAGAGAGTCATTGGTT |
| 5753 | GTTCCAAACCCATCGTCAGTGTGTGTTTAGAGCTGTGTGCACCCTAGAAACAACTACTTGTCCCATCAGCAGGTGCCTGACACAGACCCCTTTGCATTCACAGAGAGTCATTGGTT |
| 5873 | ATAGAGACTTGAATTAATAAGTGACATTATGCCAGTTTCTGTTCTTGCACTACATACTCTTCAGTGTAGAGCCTCTGTTTTATGGGAAAAGGC |
| 5993 | TCAAATGGCAAATTGTGTTGATGATTAATAATGCCCTTTTGCCGATGCATAATTACTGATGTGACATCGGTTTCTGTTCTTGCACTACATACTCTTCAGTGTAGAGCCTCTGTTTTATGGGAAAAGGC |
| 6113 | TTTGCACTTTGAAAAGAATCAGCGGATGCTCGACGCTGTAAACAATTGTGTTGATGATTAATAATGCCCTTTTGCCGATGCATAATTACTGATGTGACATCGGTTTCTGTTCTTGCACTACATACTCTTCAGTGTAGAGCCTCTGTTTTATGGGAAAAGGC |
| 6233 | TTTGCACTTTGAAAAGAATCAGCGGATGCTCGACGCTGTAAACAATTGTCAAATAAGAATTAAACTAAAAAAAAAAAAAAAAAAA |

It has been possible to observe that, by using this receptor instead of the hER receptor, a greater stability of the receptor was obtained, hence eliminating all risk of denaturation capable of leading to less binding of the specific ligand, in this instance estradiol. This phenomenon is expressly true in the region of 25° C., that is to say at the temperatures at which the method for the preparation of recombinant proteins comprising an induction stage according to the invention is carried out. It is hence preferable to use this receptor, which enables a smaller quantity of estradiol to be introduced into the culture medium in order to initiate the induction.

According to an additional feature of the invention, estradiol is added at a concentration of between 2 and 50 nM, and preferably of the order of 10 nM.

The invention relates especially to the case in which the control sequence is the sequence -605 to -634 of the chicken vitellogenin gene, which is the transcription control sequence of this gene, sensitive to estradiol (designated hereinafter ERE for "estrogen responsive element"). The synthesis of oligonucleotides containing this sequence or repetitions of the latter makes it possible to obtain, according to the invention, an expression vector comprising this sequence or repetitions of the latter (designated hereinafter ERE1 or ERE3).

One of the advantages of the invention is that the induction of the expression may be initiated very simply by adding to the culture medium a ligand matched to the receptor. The implementation of the induction hence becomes completely independent of the nature of the culture medium.

The appropriate time point for the introduction of the ligand can be determined easily; in practice, it will be the point at which a high level of biomass has been attained in the fermentation vat.

The invention relates most especially to the vectors, the structure and method for production of which will be given later by way of example in the experimental part.

It is appropriate to note that the elements for the expression of the protein and the elements providing for the expression of the receptor can occur on a single plasmid or on two different plasmids each containing an origin of replication which is functional in yeasts. However, it is also possible to arrange for the use of vectors providing for the integration of some of these elements, for example the production of the receptor can originate from sequences integrated on a chromosome of the cell.

Thus, the present invention also relates to the vectors carrying the sequences which are usable for the transformation of yeast cells.

The invention also encompasses the yeast strains which are usable in the method according to the invention.

As yeast strains, all strains customarily used for the production of recombinant proteins may be used. Saccharomyces strains such as *S. cerevisiae* may be mentioned, in particular. Special mention may be made of strains displaying one or more deficiencies in proteolytic activity, for example having the pep4 mutation. There may also be mentioned strains displaying a suppresion of the proteolytic function encoded by the PRC1 gene. The use of these strains enables the quality of the proteins obtained to be improved.

BRIEF DESCRIPTION OF DRAWINGS

FIG. 5a shows diagrammatically the result of insertion in tandem of a portion of the coding sequence of PRC1 into pUC8 (BamHI site) to give pTG2893, FIG. 5b shows schematically the deletion introduced into the fragment of PRC1 by excision of the EcoRV fragment of pTG2893 to give pTG2894, the arrows showing the direction of transcription.

The examples which follow illustrate the invention without, however, limiting the latter.

EXAMPLE 1

Construction of the PYERE/hER Vectors

Methods

The techniques of molecular biology used for the construction of the different plasmids are described in the manuals "Molecular cloning, a laboratory manual", T. Maniatis, E. F. Fritsch and J. Sambrook, Cold Spring Harbor, N.Y.: Cold Spring Harbor Laboratory (1982) and "Current Protocols in Molecular Biology", F. M. Ausubel, R. Brent, R. E. Kingston, D. D. Moore, J. A. Smith, J. G. Seidman and K. Sruhl, Greene Publishing Associates and Wiley Intersciences (1987). They comprise, in particular, digestion of the DNA with restriction enzymes, separation of the DNA fragments by agarose or polyacrylamide gel electrophoresis, ligation of DNA fragments with the enzyme T4 DNA ligase, transformation of *E. coli* with the recombinant plasmids and determination of the nucleotide sequence by Sanger's technique.

The plasmids used carry the gene for resistance to ampicillin, thereby permitting selection of the bacteria transformed by a plasmid on agar dishes containing ampicillin (50 μg/ml).

The *E. coli* strain used is strain DH5, genotype: F-, enda1, HsdR17(rk-md+), supE44, thi-1, lambda-, reca&, gyrA96, reIAI (Hanahan: DNA cloning: a practical approach (Vol. 1=p. 109–135, ed. D. M. Glover, IRL Press, Oxford (1985)).

The techniques of transformation and growth of yeast strains are described in "Laboratory Course Manual for Methods in Yeast Genetics", F. Sherman, G. R. Find and J. B. Hicks, Cold Spring Harbor, N.Y.: Cold Spring Harbor Laboratory (1986).

The yeast strain used is TGY14-1a, pep4.3, genotype Mat a, ura3-251-373-328, leu2, pep4.3.

Figure 1:
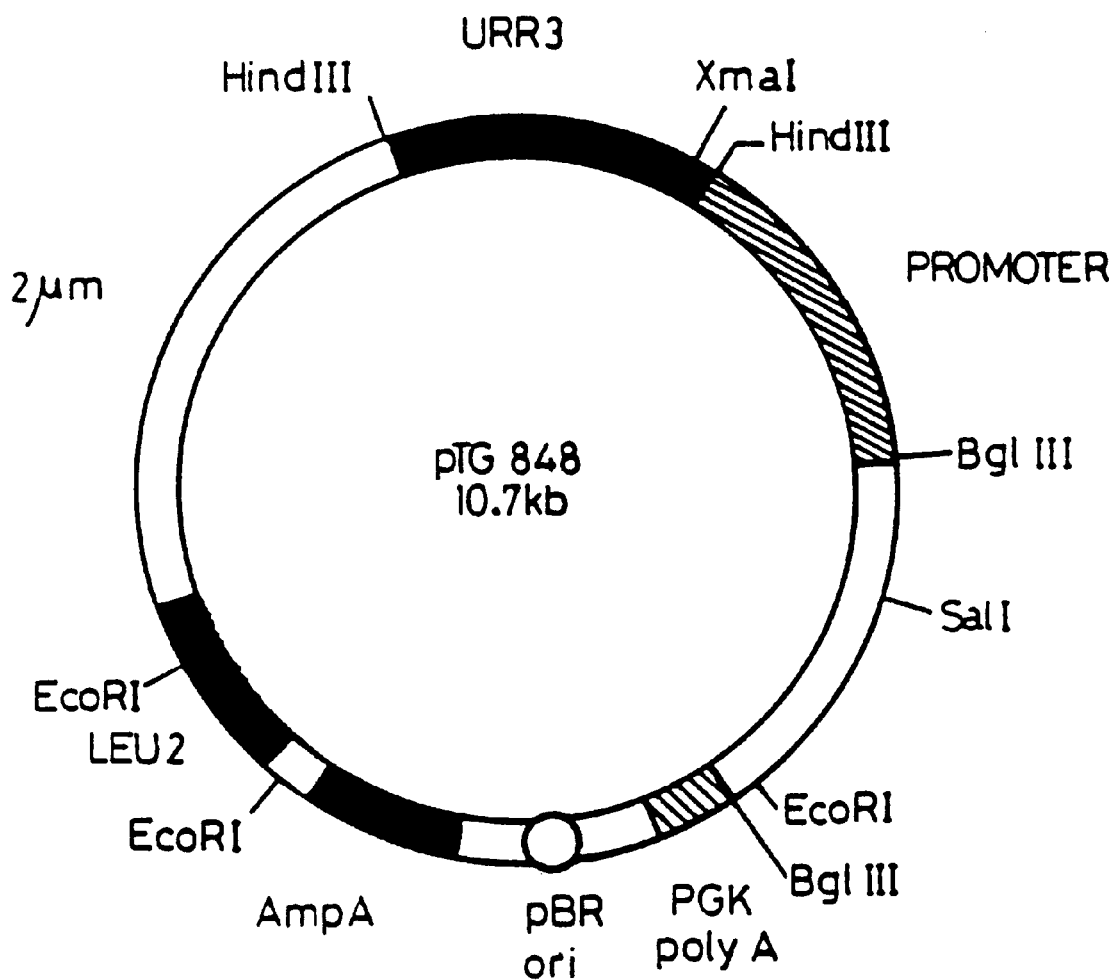
FIG. 1 shows the structure of pTG848.

The parent plasmid pTG848, described in European Patent No. 200,655, is an *E. coli*/yeast shuttle plasmid which permits the expression in yeast of an exogenous gene under the control of the phosphoglycerate kinase (PGK) gene promoter. This plasmid contains a pBR 322 origin of replication and the gene for resistance to ampicillin for selection in E. coli, and a 2 μm origin of replication and the ura3 and leu2 genes for selection in yeast, as well as the PGK gene promoter and its 3' end containing the polyadenylation signal. This gene was modified so as to introduce a BglII site at the initiation ATG, thereby enabling the coding region for another protein to be inserted between this site and the BglII site situated upstream from the polyadenylation signal (FIG. 1).

Construction of Plasmids pUC18, ERE1, DUC18 EREm, pUC18 ERE3

Plasmid pUC18 (C. Yanisch-Perron, J. Vieira and J. Messing, Gene 33, 103–1190 (1986)) contains a pBR322 origin of replication, the gene for resistance to ampicillin and a polylinker comprising, in particular, XbaI and HindIII sites. This plasmid was digested with the restriction enzymes XmaI and HindIII; to the plasmid thus digested, the following are then added by complementary oligonucleotide techniques:

5'-CCGGGTCTAGAAGATCTA3' (SEQ ID NO: 3)
3'-CAGATCTTCTAGATTCGA5' (SEQ ID NO: 4)

The derived plasmid pUC18 BglII then has a polylinker which contains, in order, XmaI, XbaI, BglII and HindIII sites.

Into this plasmid, digested with BglII, the fragments consisting of the following complementary oligonucleotides are introduced respectively:

ERE1:

5'GATCCAATATTCCTGGTCAGGCGTGAC-CGGAGCTGA3' (SEQ ID NO: 5)
3'GTTATAAGGACCAGTCGCACTGGCCTC-GACTCTAG5' (SEQ ID NO: 6)

EREm:

5'GATCCAATATTCCCCGTCAGCGTGACCG-GAGCTGA3' (SEQ ID NO: 7)
3'GTTATAAGGGGCAGTCGCACTGGCCTC-GACTCTAG5' (SEQ ID NO: 8)

ERE3 which consists of a direct repetition of three ERE1 fragments.

ERE1 contains the ERE (for "estrogen responsive element") sequence -605 to -634 of the vitellogenin promoter.

EREm is a mutant in which a GC transversion in the ERE sequence considerably reduces its activity in MCF-7 cells.

Construction of Plasmids pLRERE1, PLREREm, pLRERE3

Figure 2:
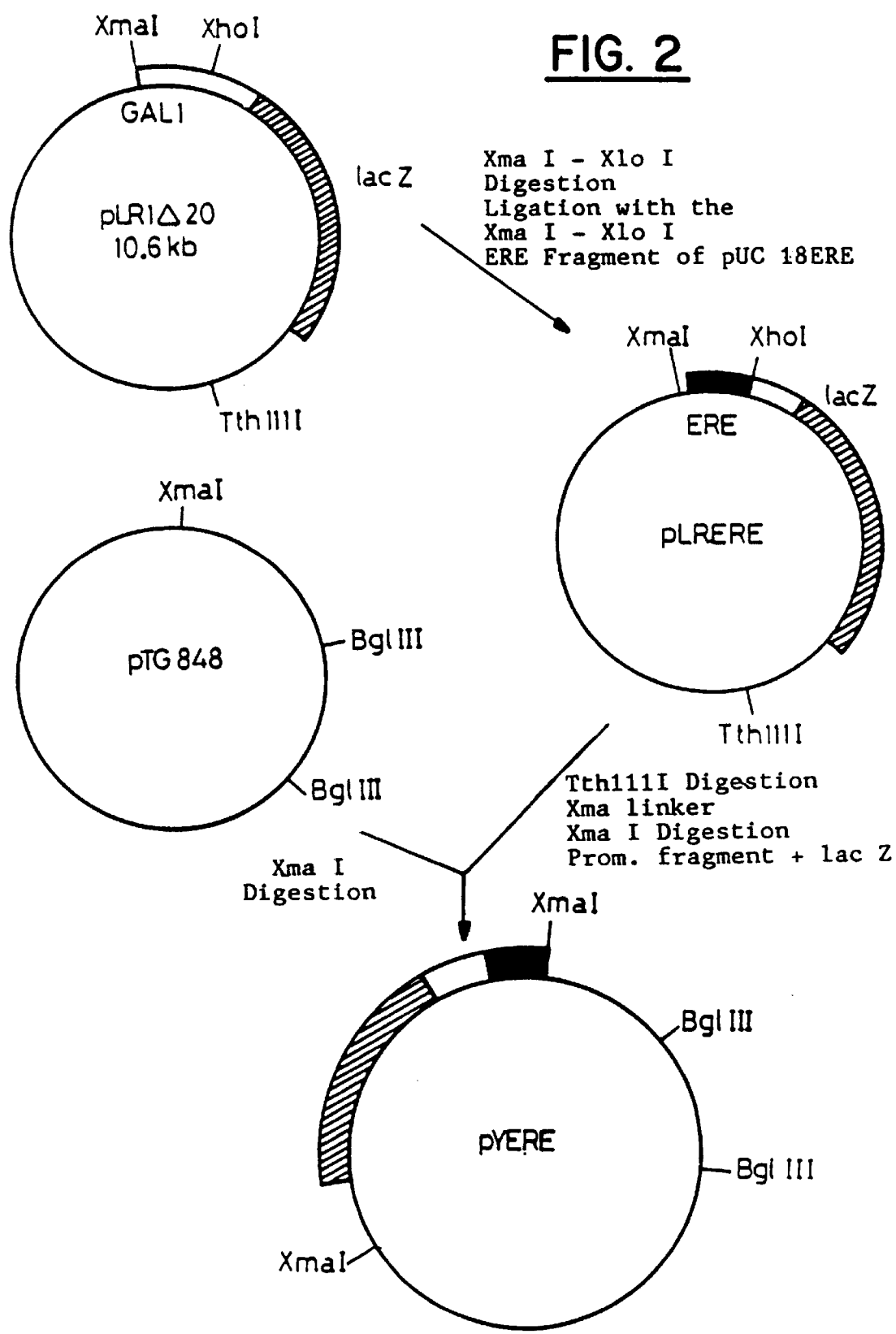
FIG. 2 shows schematically the strategy enabling pYERE to be prepared.

Plasmid pLR1Δ20 is described in the paper by R. W. West, R. R. Yocum and M. Ptashne, Molecular and Cellular Biology 4, 2467–2478 (1984). This plasmid contains an active and chimeric gene for beta-galactosidase under the control of the GAL1 promoter (FIG. 2).

The object of the construction is to replace the UASs (upstream activator sequences) of the Gal1 gene, situated between the XmaI and XhoI sites of the Gal1 promoter region, by the fragments ERE1, EREm and ERE3, respectively.

pLRERE1

Plasmid pUC18ERE1 is digested with the restriction enzyme BglII. The site is filled in with DNA polymerase I (Klenow fragment) in the presence of the 4 deoxynucleotide triphosphates. An XhoI linker (Biolabs ref. 1030) is then added to the ends: the plasmid is then digested with XmaI and XhoI and the XmaI-XhoI fragment containing the ERE1 sequence is isolated.

This fragment is then cloned into plasmid pLR1Δ20 between XmaI and XhoI sites to give plasmid pLRERE1.

pLREREm, pLRERE3

Plasmids pLREREm and pLRERE3 are constructed in the same manner by replacing pUC18ERE1 by pUC18EREm and pUC18ERE3, respectively, in the above protocol.

Construction of Plasmids pYERE1, pYEREm, pYERE3

Plasmids pLRERE1, pLREREm and pLRERE3 possess a Tth111I site at the 3' end of the lacZ (beta-galactosidase) chimeric gene (FIG. 2).

pYERE1

Plasmid pLRERE1 is digested with the enzyme Tth111I; the site is then filled in with DNA polymerase I (Klenow fragment). An XmaI linker (Biolabs ref. 1048) is then added to the ends. The DNA is digested with XmaI, and the XmaI-XmaI fragment containing the lacZ chimeric gene under the control of the hybrid promoter (EREA-Gal1) is inserted at the single XmaI site of plasmid pTG848, to give plasmid pYERE1.

pYEREm, pYERE3

Plasmids pYEREm and pYERE3 are constructed in the same manner by replacing pLRERE1 by pLREREm and pLRERE3, respectively, in the above protocol.

Construction of Plasmid pYGAL

Plasmid pLR1Δ20 is digested with the restriction enzyme Tth111I, and the site is then filled in with DNA polymerase I (Klenow fragment). An XmaI linker (Biolabs ref.1048) is added to the ends and the DNA is then digested with the enzyme XmaI. The XmaI fragment containing the lacZ chimeric gene under the control of the Gal1 promoter is inserted at the XmaI site of plasmid pTG848, giving plasmid pYGAL.

Construction of Plasmids pYERE1/hER, pYERE1/hERR, pYEREm/hER, pYGAL/hER

Figure 3:
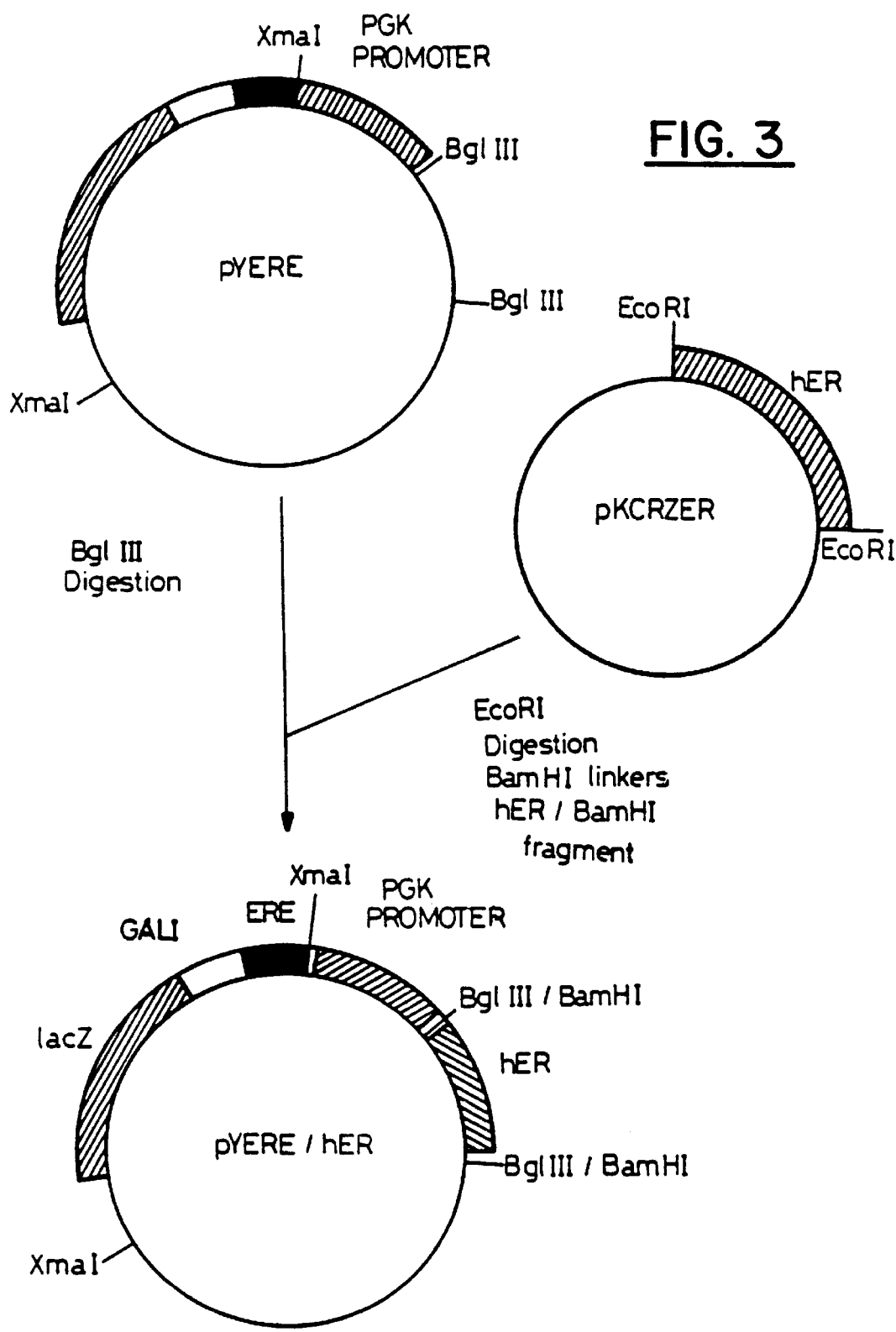
FIG. 3 shows schematically the strategy enabling pYERE/hER to be prepared.

The object of these constructions is to place the cDNA coding for the human estrogen receptor (hER) under the control of the PGK promoter, at the BglII site of plasmids pYERE1, pYEREm, pYERE3 and pYGAL (FIG. 3).

Plasmid pKCR2-ER containing the cDNA of the human estrogen receptor (S. Green et al., Nature 320, 134–139 (1986)) is digested with the restriction enzyme EcoRI and the site is then filled in with DNA polymerase I (Klenow fragment). A BamHI linker (Biolabs ref. 102) is then added to the ends. After digestion with BamHI, the fragment coding for the human estrogen receptor is isolated.

It is inserted into the vector pYERE1 digested with BglII to create plasmids pYERE1/hER and pYERE1/hERR, which differ by the orientation of the hER cDNA relative to the PGK promoter.

In pYERE1/hER, the PGK promoter is situated on the 5' side of the hER cDNA, and hence induces transcription of the mRNA coding for the hER protein.

In pYERE1/hERR, the orientation is reversed, and hence induces the transcription of an antisense RNA of the hER messenger RNA.

pYEREm/hER, pYERE3/hER and pYGAL/hER are constructed on the same model as pYERE1/hER, by replacing pYERE1 by pYEREm, pYERE3 and pYGAL, respectively, in the above construction.

Figure 4A:
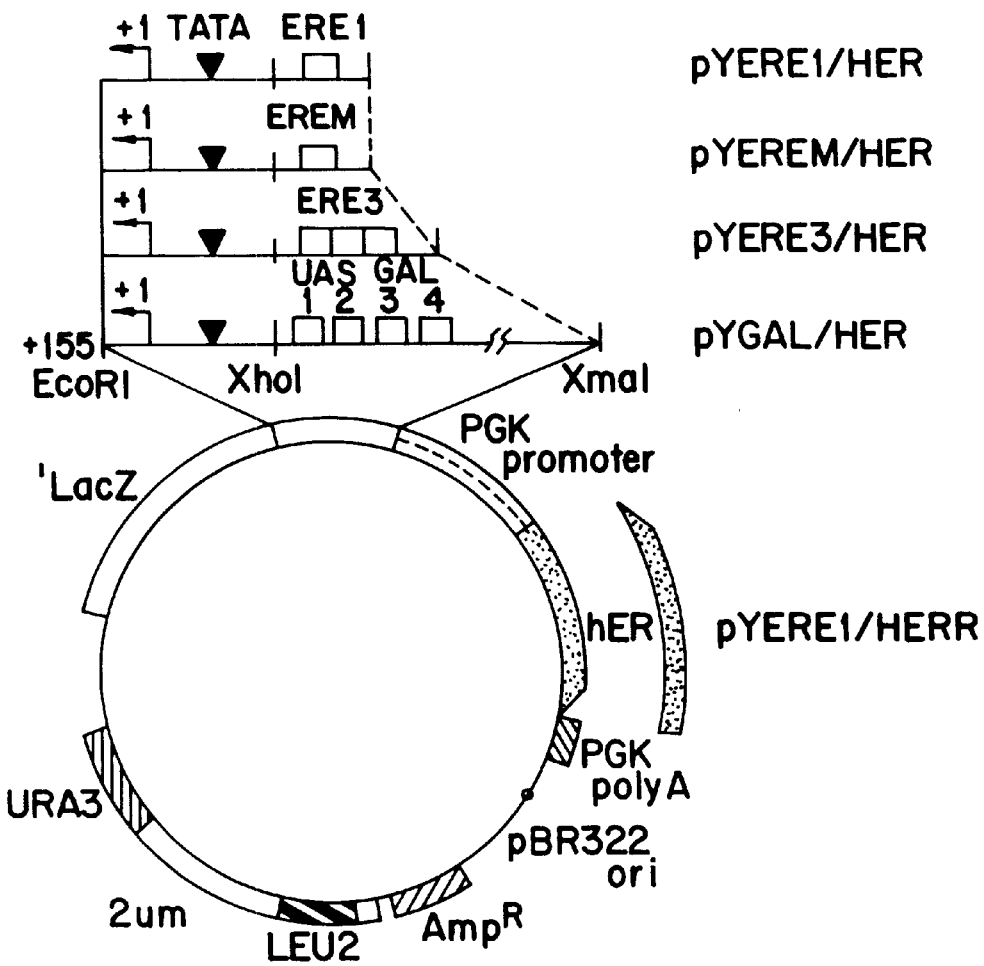
FIG. 4a shows schematically the structures of pYERE1/hER, pYEREm/hER, pYERE3/hER and pYGAL/hER and shows the sequences of the ERE and EREm elements.

These plasmids (FIG. 4a) constructed in E. coli DH5 are transferred into yeast strain TGY14.1a which carries the ura3 mutation. The presence of the ura3 gene on these plasmids permits complementation for the yeasts transformed by a plasmid, which are hence selected on agar dishes containing a medium without uracil (preparation: 0.67 g of Difco medium No. 0919-15, 0.5 g casamino acids, 1 g glucose, and 2 g agar per 100 ml).

EXAMPLE 2

Figure 4B:
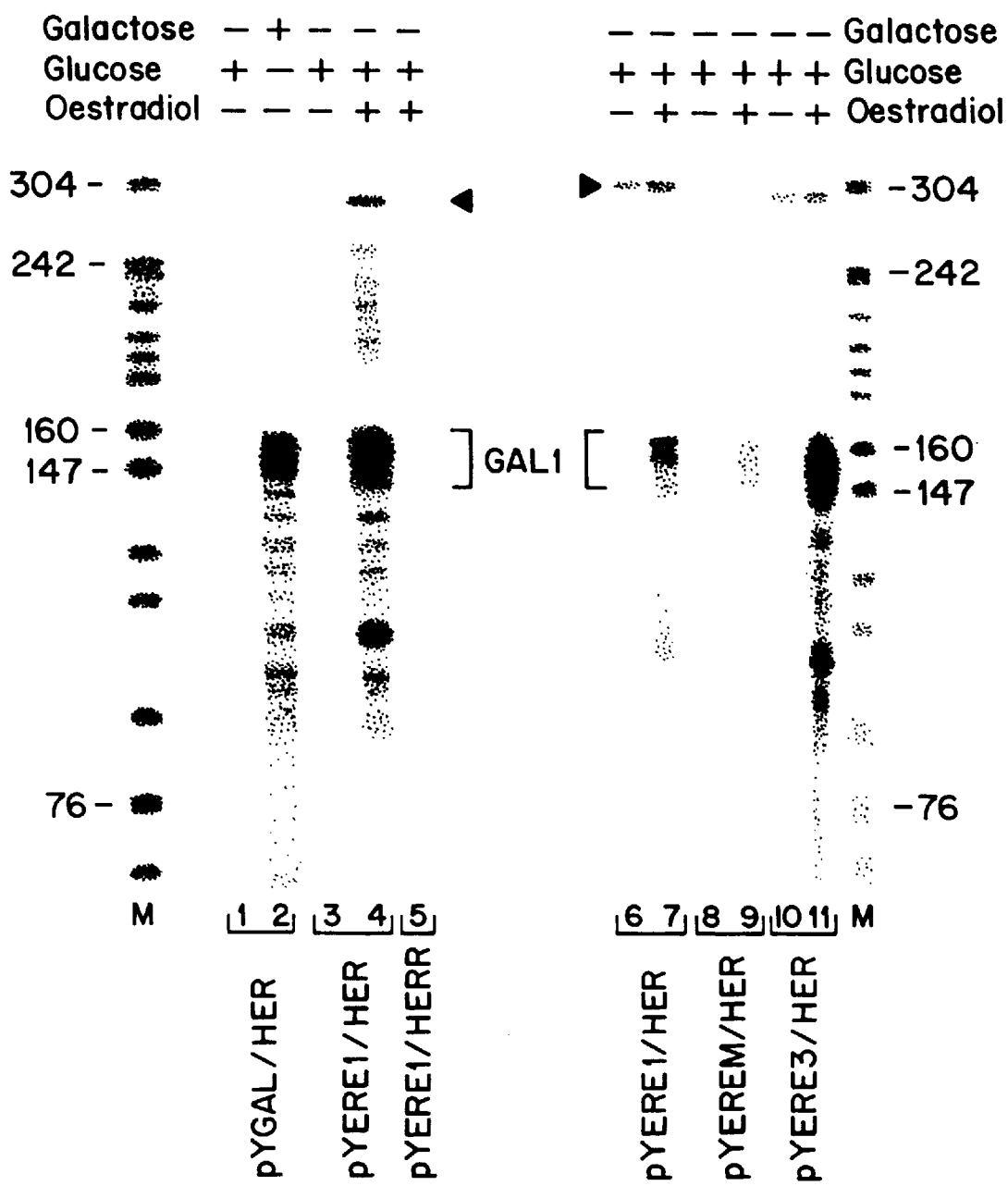
FIG. 4b shows, for the RNAs extracted from induced or noninduced cells containing the plasmids indicated, the RNA fragments protected from digestion by ribonucleases A and T1 after hybridization with an antisense Gal1 RNA probe.

Induction by Estradiol of Transcription for the ERE Gal1 Hybrid Promoters Carried by the pYERE/hER Vectors The different yeasts containing plasmids pYERE1/hER, pYEREm/hER, pYERE3/hER, pYERE1/hERR and pYGAL/hER, respectively, are cultured in base medium for yeast (Difco No. 0919-15) on the basis of 0.67 g/100 ml and 0.5% casamino acids containing 1% glucose or 2% galactose or 100 nM estradiol (added to the culture 2 hours before the cells are recovered) as shown in FIG. 4b.

The RNA is prepared from $10^9$ cells according to the protocol described in Methods in Yeast Genetics, p. 143–144.

To measure the transcriptional activity of the Gal1 or ERE-Gal1 promoters, these RNAs are hybridized with a radiolabeled RNA probe derived from the 5' end of the Gal1 gene (strand complementary to the messenger RNA). The hybridized fragments will be protected from digestion by RNases A and T1. The probe is prepared from the EcoRI fragment (containing the Gal1 promoter) of plasmid pLR1Δ20 (R. W. West, R. R. Yocum and M. Ptashne, Molecular and Cellular Biology 4, 2467–2478 (1984)) cloned into plasmid Bluescribe M13+ (Stratagene ref. 211201). The resulting plasmid is then linearized with HindIII and the radiolabeled probe is then synthesized from the phage T7 promoter with Stratagene Kit No. 211604. The probe size is of the order of 1000 nucleotides.

There are several transcription initiation sites in the Gal1 promoter; the probe is complementary to the Gal1 RNA over a length of 154 to 165 nucleotides.

The probe is incubated with 20 μg of RNA, and the mixture containing possible hybrids is digested with ribonucleases A and T1 according to the protocol described in Current Protocols in Molecular Biology.

The undigested fragments are then identified by urea/polyacrylamide gel electrophoresis and autoradiography (FIG. 4b).

For the constructions expressing the hER receptor, the induction of a messenger RNA specific to the ERE-Gal1 hybrid promoter is observed in the presence of estradiol; the transcription initiation sites are identical to those of the Gal1 (pYGAL) promoter induced by galactose: protected fragments of the same size.

The induction of transcription using the ERE-Gal1 hybrid promoter is strictly dependent on the presence of estradiol. The induction by estradiol requires the presence of the hER receptor (the construction pYERE/hERR is inactive). It also requires the presence of an ERE element (for the construction pYGAL/hER, there is no induction by estradiol).

The quantity of Gal1 RNA detected for cells containing pYERE3/hER is approximately 10 times as high as for cells containing pYERE1/hER: the repetition in tandem of the ERE elements (pYERE3 contains an ERE trimer, pYERE1 a monomer) hence appears to have a synergistic effect on the activation of transcription.

EXAMPLE 3
Expression, Inducible by Estradiol, of Beta-galactosidase in Yeasts Containing the pYERE/hER Vectors Beta-galactosidase activity is measured according to the protocol of West et al. (1984). Table 1 below shows the beta-galactosidase activity of yeast strains carrying plasmids pYERE1/hER, pYERE3/hER, pYEREm/hER, pYERE1/hERR and pYGAL/hER, respectively, in the presence or absence of glucose, galactose or estradiol, as seen in the table.

The level of constitutive activity of the promoters is very low and is not affected by the presence of the hER protein (pYGAL and pYGAL/hER or pYERE1/hER and pYERE1/hERR give the same degree of activity). In contrast, the addition of estradiol leads to a strong induction of the hybrid promoters of pYERE1/hER and pYERE3/hER.

The fact that the promoters of pYEREm/hER and pYGAL/hER are not sensitive to induction by estradiol shows the necessity of a functional ERE element in the promoter controlling the expression of lacZ, while the absence of induction for pYERE1/hERR shows that the presence of the hER receptor is also necessary for observing induction by estradiol.

The level of expression attained in comparable to that obtained using the Gal1 promoter (the case of pYGAL/hER) in the presence of galactose.

The presence of three ERE elements in tandem (the case of pYERE3/hER) gives an activity twice as high as the case where the promoter contains a single ERE element (pYERE1/hER).

TABLE 1

Induction of beta-galactosidase activity by YhER in the presence of hormone

| PLASMID | MEDIUM | | | BETA-GALACTO-SIDASE ACTIVITY (units) |
| --- | --- | --- | --- | --- |
| | Glucose | Galactose | Estradiol | |
| pYERE1/hER | + | − | − | 60 |
| pYERE1/hER | + | − | + | 1,060 |
| pYERE1/hERR | + | − | − | 60 |
| pYERE1/hERR | + | − | + | 60 |
| pYERE3/hER | + | − | − | 60 |
| pYERE3/hER | + | − | + | 2,060 |
| pYEREM/hER | + | − | − | 60 |
| pYEREM/hER | + | − | + | 260 |
| pYGAL/hER | + | − | − | 180 |
| pYGAL/hER | + | − | + | 180 |
| pYGAL | + | − | − | 180 |
| pYGAL | − | + | − | 2,300 |

The yeasts transformed by the plasmids indicated are cultured in the presence of 1% of glucose or 2% of galactose as stated in the table; for induction by estradiol, 100 nM hormone is added 2 hours before the cells are harvested.

The tests of beta-galactosidase activity are performed in a traditional manner (West R. W. jr., Yocum R. R. and Ptashne M., Mol. Cell. Biol., 4, 2467–2478 (1984)).

EXAMPLE 4
Integration of a Complementary DNA Coding for hER in the Genome of a Yeast Strain
Preparation of the Expression Vector Carrying a Cassette for the Expression of hER Inserted into the PRC1 Gene (pTG3809)

The cassette for the expression of hER is inserted into a fragment of the PRC1 gene in order to obtain, after transformation of a yeast strain with pTG3809, a yeast strain displaying elimination of the proteolytic function encoded by the PRC1 gene.

In the first place, a cassette for the expression of hER (M13TG2896) is prepared in the following manner:

the yeast PGK promoter (HindIII-BglII fragment) and its terminator (HindIII-BglII fragment) are introduced into phage M13TG130 (Kieny, M. P. et al. (1983), Gene 26, p. 91–99) linearized by HindIII digestion, to give phage M13 TG2890, the BamHI fragment derived from pKCR2-hER carrying the human estrogen receptor is introduced into M13TG2890 linearized by BglII digestion, to give a cassette for the expression of hER referred to as M13TG2896.

This cassette for the expression of hER is then inserted into the PRC1 gene to give plasmid pTG3809 permitting its integration in the yeast genome.

The sequence of the PRC1 gene has been published by Valls, L. A. et al. (1987) (Cell 48, p. 887–897). Two oligonucleotides are constructed from this sequence. The first is complementary to the 5' region of the gene, and its sequence is as follows:

5' AAG AAA GAC TGG GAC TTT GTG 3' (SEQ ID NO: 9)

The second is complementary to the 3' region of the gene, and its sequence is as follows:

5' GAT TGG ATG AAG CCT TAC CAC 3' (SEQ ID NO: 10)

From a yeast genomic library (chromosomal DNA fragments partially digested with Sau3A, inserted into the BamHI site of pFL1 (Parent, S. A. et al. (1985), Yeast 1, p. 83–138)), and by hybridization with these two oligonucleotides, an *E. coli* clone containing the PRC1 gene inserted into pFL1, and referred to as pTG2863, is selected.

The 1.1-kb BamHI fragment of pTG2863 carrying a portion of the coding sequence of the PRC1 gene is introduced into the BamHI site of plasmid pUC8. This insertion takes place in tandem and plasmid pTG2893 (FIG. 5a) is obtained.

The coordinates of the first base of the restriction sites, relative to the adenine of the ATG of the PRC1 coding sequence, are as follows: BamHI-1: 482; EcoRV-1: 1102; EcoRV-2: 1153; EcoRV-3: 1234 and BamHI-2: 1574.

A deletion in the PRC1 coding sequence is accomplished by EcoRV digestion of pTG2893 to give pTG2894 (FIG. 5b).

Figure 6:
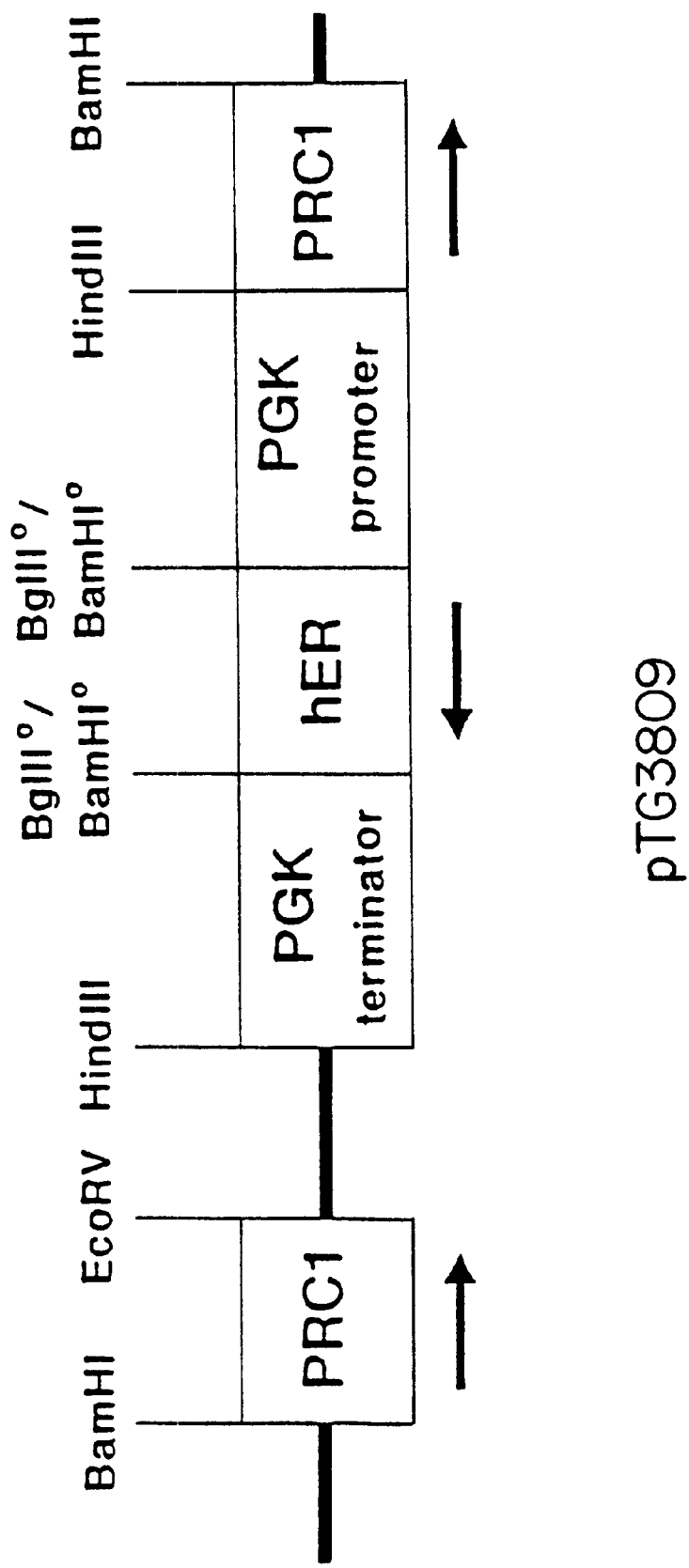
FIG. 6 shows the diagrammatic structure of plasmid pTG3809, the arrows showing the direction of transcription.

The cassette for the expression of hER is introduced into the deleted inner fragment of the PRC1 gene of pTG2894 in the following manner: the expression cassette (M13TG2896) is digested with BamHI, the ends are filled in with Klenow polymerase and, after cleavage with EcoRV, fragment is isolated. This fragment carries the complete cassette; it is introduced into the EcoRV site of pTG2894 to give plasmid pTG3809 (FIG. 6), which carries, between two fragments of PRC1:

several recognition sites for the restriction enzymes SphI, XbaI and KpnI originating from M13TG130,
the PGK terminator yeast,
the complementary DNA of hER,
the PGK promoter of the yeast.

Transformation of the Yeast Strain with the Plasmid Carrying the hER Expression Cassette Inserted into a Fragment of the Deleted PRC1 Gene (pTG3809)

The yeast strain transformed is *S. cerevisiae* TGY2sp13b (MATa; ura3-251, -373, -328; leu2-3, -112).

Plasmid pTG3809 is cleaved with BamHI. The DNA sequences of the ends of the fragment thereby isolated are homologous with those of the PRC1 gene sequence. These sequences will enable the fragment to be integrated in the genomic portion of the PRC1 gene of the yeast strain. This insertion leads to destruction of the genomic PRC1 gene by deletion.

Since the fragment does not carry a selection marker, plasmid pLRERE3 is used as a cotransformation vector. It permits the selection of Ura$^+$ prototrophs. Among Ura$^+$ prototrophs, the clones which have integrated the hER expression cassette carry a mutation in the PRC1 gene which leads to a loss of activity of carboxypeptidase yscY. These mutants are detected by a colorimetric test (Jones, E. W. (1977), Genetics 85, p. 23–33). The structure of the modified PRC1 locus is verified by Southern's method.

This *S. cerevisiae* strain which has integrated the cassette for the expression of hER in the deleted PRC1 gene is referred to as TGY2sp13b prc1-d :: hER.

Construction of a Plasmid Carrying the ERE3 Sequence and a Fragment of the PGK Gene Promoter (pGT3851)

Figure 7:
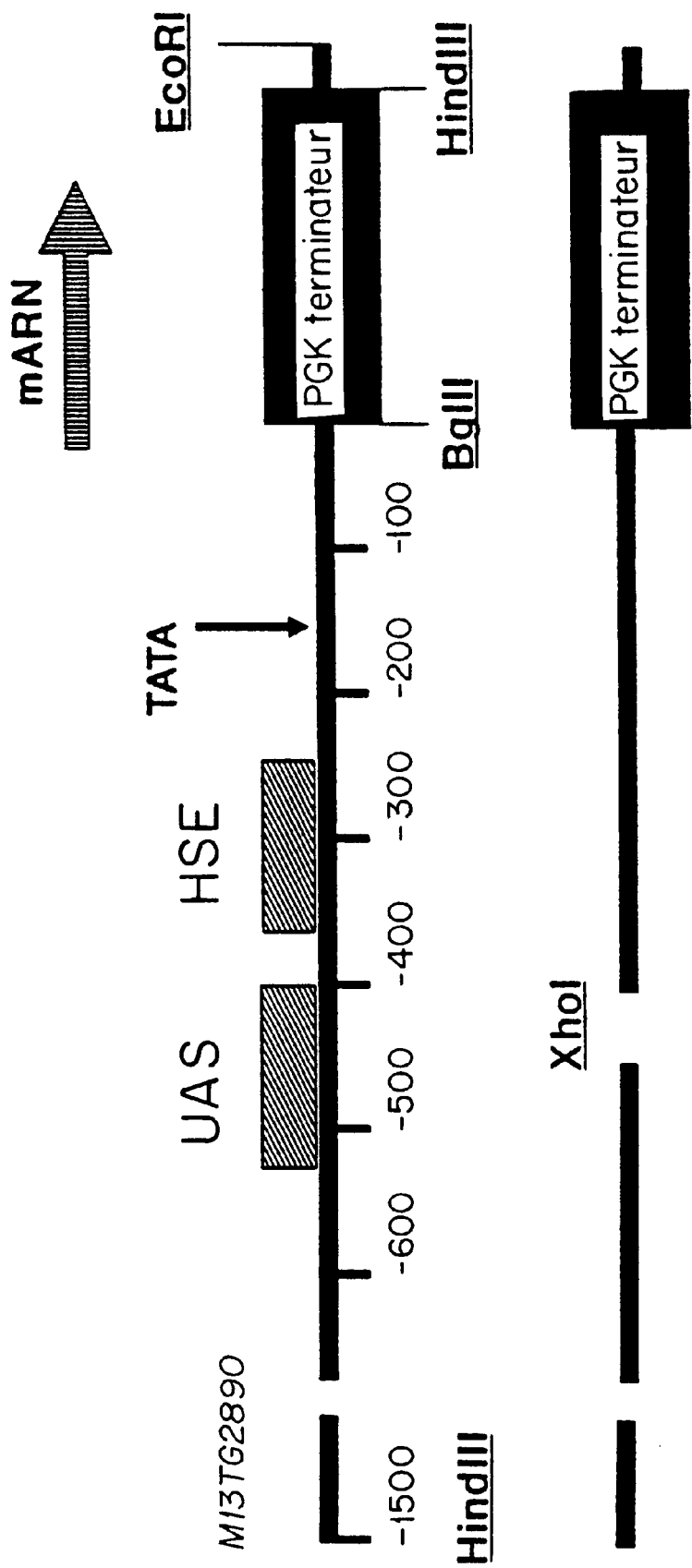
FIG. 7 shows the diagrammatic structure of phage M13TG2890.

An XhoI site is introduced into the vector M13TG2890 at the 5', 3' junction of the ends of the deletion accomplished by direct mutagenesis using the following oligonucleotide:
-506 . . . -401
5' AATTACCGTCGCTCG AGCGACGGCTCACAG 3' (SEQ ID NO:11)
XhoI to give the vector M13TG3829 (FIG. 7). The positions indicated are specified relative to the ATG of the PGK gene. The deleted form of the PGK promoter will be designed hereinafter PGK-dp401. The conformity of the sequence is then verified by sequencing.

This vector carries the TATA sequence and the transcription initiation site, the second activator sequence downstream designated HSE from -256 to -377 (Piper, P. W. et al. (1988), Nucleic Acids Res. 16, p. 1333), but no longer carries the UAS from -402 to -479. The XhoI site permits ligation with the ERE3 sequence, and the BglII site the introduction of a gene which enables an activity to be detected by an enzymatic test.

The host strain for the M13 phages is *E. coli* strain JM103 (delta(lac, pro), thi, strA, supE, endA, sbcB, hsdR, F'traD36, proAB, lacIQ, lacZdeltaM15).

Plasmid pLRERE3 is digested with XmaI and EcoRI. The DNA fragment containing the ERE3 sequences is purified on agarose gel and then inserted into the XmaI-EcoRI sites of plasmid pTZ18R (Pharmacia, LKB Biotechnology) to give plasmid pTG3833. The host strain for the plasmids is *E. coli* strain 1106 (supE, hsdR, hsdM, met, supF).

Phase M13TG3829 (FIG. 7) is treated with XhoI and EcoRI and is then inserted at the XhoI-EcoRI site of plasmid pTG3833 to give pTG3834.

The lacZ gene is excised from pCH110 (Hall, C. V. et al. (1983), J. Mol. Appl. Gen. 2, p. 101–109) by HindIII-BamHI digestion and cloned into pPolyII (Lathe, R. et al. (1987), Gene 57 p. 193–201) to give pTG1174. Plasmid pTG2145 corresponds to plasmid pTG1174 in which the HindIII, PstI and SalI sites have been eliminated. It contains, in a BglII-BamHI fragment, the following *E. coli* gene fusion: gpt :: trDS :: lacZ.

The sequences in the vicinity of the ATG are modified so as to permit the correct translation in yeast in the following manner:

pTG2145 is digested with BglII and KpnI and the 200-base pair fragment containing the ATG is purified on acrylamide gel;

this fragment is inserted at the BamHI-KpnI sites of phage M13TG131 (Kieny, M. P. et al. (1983), Gene 26, p. 91–99) to give M13TG3838;

the "AGC" sequence corresponding to the second codon for a serine of M13TG3838 is exchanged for the sequence "TCT", the cytosines at positions -3 and -1 relative to the ATG are replaced by adenines and a BglII site is generated on the 5' side of the ATG to permit a fusion with genes to be inserted downstream from the hybrid promoter, by performing a directed mutagenesis using the following oligonucleotide:

5' C G A T G T A T T T T T C A G A C A T T T T A A-GATCTCCAGCCTGTTT 3' (SEQ ID NO: 12) to give phage M13TG3842. The bases modified during this mutagenesis are underlined below:

GACACTTCACATGAGC- (M13TG3838) (SEQ ID NO: 14)

AGATCTTAAAATGTCT- (M13TG3842) (SEQ ID NO: 15)

The 130-base pair BglII-KpnI fragment of M13TG3842 is introduced into pTG2145 to replace the 200-base pair BglII-KpnI fragment therein. Plasmid pTG3843 is thereby obtained.

Plasmid pTG848 (FIG. 1) is digested with BglII and then religated to give pTG2886. The large HindIII-EcoRI fragment of pTG2886 is ligated in the presence of T4 ligaseth BwlII and thHindIII-EcoRI fragment of plasmid pFL1 (Parent S. A. et al. (1985), Yeast 1, p. 83–138) which carries a sequence of the *S. cerevisiae* plasmid, to give plasmid pTG2886 LEU2-d, URA3-d. The 0.9-kb HindIII fragment of plasmid pTG2800 described in the European publication of Patent EP-A-0,258,501 carrying the URA3-d gene is then inserted into the HindIII site of this plasmid to give pTG2886 URA3-d, delta LEU2-d. The SmaI-BglII fragment of M13TG131 (Kieny, M. P. et al. (1983), Gene 26, p. 91–99) which possesses several restriction sites is then introduced into this plasmid to give pTG3828.

Plasmid pTG3843 is digested with BglII and BamHI, and the fragment carrying the lacZ fusion gene is purified on agarose gel. This fragment is then inserted at the BglII site of pTG3846 (FIG. 8).

Figure 8:
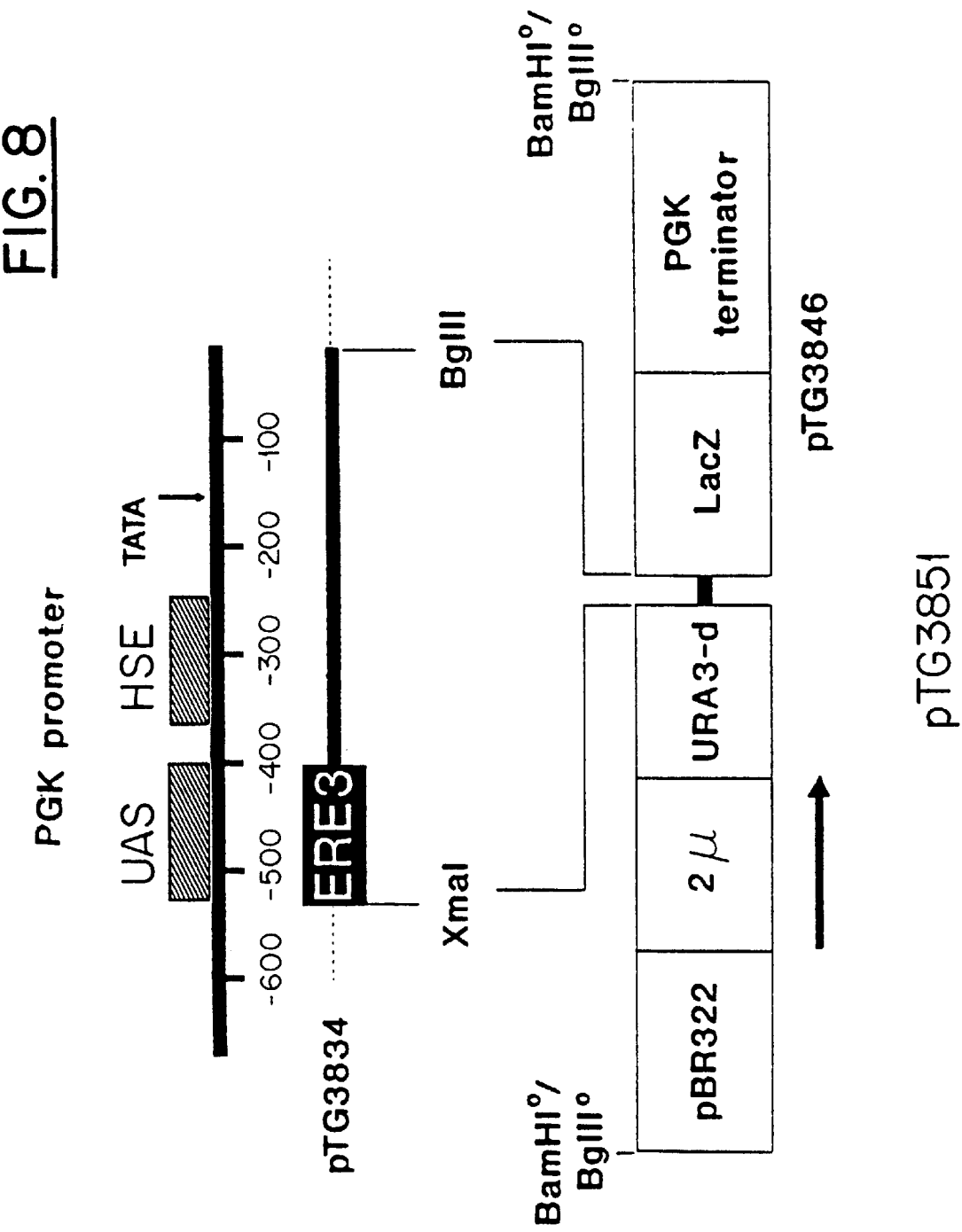
FIG. 8 shows diagrammatically the construction of plasmid pTG3851, FIG. 9 demonstrates the effect on the activation of transcription in yeast cells of adding increasing quantities of estradiol with, as receptor, either the human estrogen receptor hER (circles) or the human estrogen receptor hERG (triangles).

The plasmid pTG3834 is digested with XmaI and BglII, and the fragment is introduced into the XmaI and BglII site of pTG3846 to give plasmid pTG3851 (FIG. 8).

Inducible Expression of lacZ

*S. cerevisiae* strain TGY2sp13b prc1-d :: hER is relieved of its cotransformation plasmid pLRERE3 and then transformed with plasmid pTG3851 by the lithium acetate method (Ito, H. et al. (1983), J. Bacteriol. 153, p. 163–168), and the Ura$^+$ prototrophs are selected. They are then cultured in an Erlenmeyer at 30° C. on a selective medium (0.7% of nitrogenous bases for yeasts without amino acids (Yeast Nitrogen Bases), 0.5% of casamino acids, 2% of glucose and, if necessary, 2% of agar). These cultures are set up with or without estradiol. For induction with estradiol, 100 nM hormone is added 2 hours before the cells are harvested. The cells are harvested, washed and ground in the presence of protease inhibitors, and the cell debris is then precipitated by centrifugation (10,000 rpm). The protein concentration is determined in the supernatant by the method described by Bradford (1976) (Anal. Biochem. 72, p. 248), and then the beta-galactosidase activity by the same assay method as that described in Example 3. The beta-galactosidase activity is also determined by the method used in Example 3; the assay is performed on permeabilized cells.

Table 2 shows the basal activity (in the absence of estradiol, [−(Est)]) and induced activity (in the presence of estradiol, [+(Est)]) of beta-galactosidase under the control of the ERE3 :: PGK-dp hybrid promoters. This activity is expressed as nmol of ONPG (O-nitro-phenyl-beta-D-glucopyranoside) hydrolyzed per minute and per mg of protein at 30° C.; the values in brackets are directly comparable with those shown in Table 1, expressed in "units".

The inducibility corresponds to the ratio specific activity without estradiol/specific activity with estradiol.

TABLE 2

| Vector: PGK | Specific activity | | Inducibility |
|---|---|---|---|
| | − (Est) | + (Est) | |
| promoter pTG3851:PGK-dp401 | 20 (30) | 460 (770) | 23 |

EXAMPLE 5

Preparation of a Vector for the Expression of Beta-galactosidase in Yeast which Also Carries a Sequence Coding for the hERG Receptor (pYERE1/hERG)

The starting material is plasmid pYERE1/hER. Using the following oligonucleotide:

5'GGAGCACCCAGGGAAGCTACTGT-3' (SEQ ID NO: 13)

A mutation in the GTG codon coding for valine in the complementary DNA coding for the human estrogen receptor (hER) is produced by localized mutagenesis in the following manner: the complementary DNA coding for the hER receptor described by Green et al. (1986) (Nature 320, p. 134–139) is subcloned into the EcoRI site of the eukaryotic expression vector pSG1 described by Green et al. (1988) (Nucl. Acids Res. 16, p. 369). The single-stranded DNA is then prepared and a point mutation is produced by localized mutagenesis in the GTG codon coding for valine at position 400 so as to obtain a GGG codon coding for glycine, using the oligonucleotide defined above (the change in nucleotide is underlined). The DNA sequences are verified. The vector pYERE1/hERG is then constructed by inserting the hERG complementary DNA into the vector pYERE1/hER.

EXAMPLE 6

Figure 9:
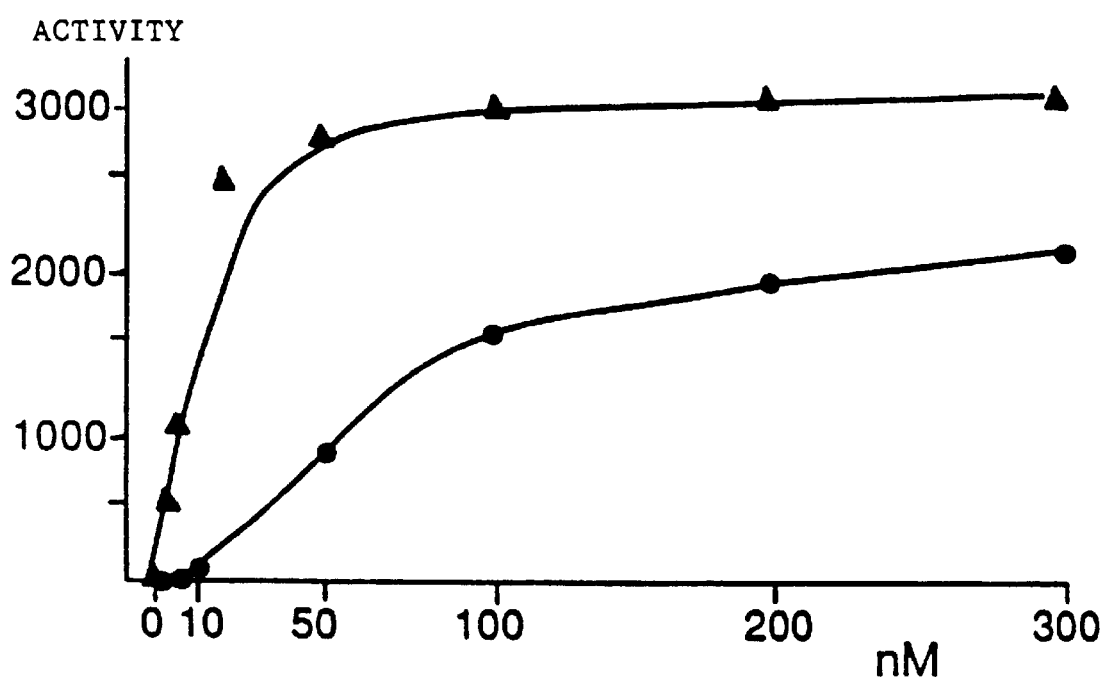

Expression, Inducible by Estradiol, of Beta-galactosidase in Yeasts Containing the Vector pYER1/hERG The conditions of transformation and culturing of the cells are identical to those described above. When the optical density reaches 600, 10 nM estradiol is added. FIG. 9 shows that 50% of the maximal beta-galactosidase activity is obtained for an estradiol concentration of 5 nM with pYERE1/hERG (triangles), whereas with pYERE1/hER (circles) a concentration of approximately 50 nM is required.

Moreover, it was possible to observe that the mutation which replaces val-400 by gly-400 in the estradiol-binding domain stabilizes the structure of the receptor and increases its affinity for estradiol to 25° C.

Saccharomyces strain TGY 14-1a pYERE3/hER was deposited with the Collection Nationale de Cultures de Microorganismes (CNCM) (National Collection of Microorganism Cultures) of the Institut Pasteur—25 rue du Docteur-Roux, 75724 Paris Cédex 15 (France) on Jun. 17, 1988 under No. I-770.

What is claimed is:

1. A method of preparing a heterologous protein that comprises:
   i) transforming a yeast cell with:
      a) a first DNA fragment encoding said heterologous protein under control of elements providing for expression of said first DNA fragment in yeast, said elements comprising a higher eucaryotic positive transcription control sequence selected from the group consisting of a natural ligand responsive element activating sequence or a variant of a natural ligand responsive element activating sequence which is a palindromic sequence or a repetition of a palindromic sequence and which retains the function of a natural ligand responsive element activating sequence in a test of inducible expression of β-galactosidase in yeast, that is induced by a higher eucaryotic receptor complexed with a ligand, and
      b) a second DNA fragment that is functional in yeast and that encodes said receptor under control of elements providing for expression of said receptor in yeast, wherein said receptor is a natural nuclear receptor selected from the group consisting of receptors for steroids or for retinoids or for thyroid hormones or for vitamin D3, and variants of said receptors which retain the function of said receptors in yeast, wherein said receptor comprises a first fragment that recognizes said ligand and a second fragment that binds to said transcriptional control sequence;
   ii) culturing said transformed yeast cell resulting from step (i) in the presence of said ligand complexed with the said expressed receptor whereby said transcription control sequence is induced and said heterologous protein is thereby produced; and
   iii) isolating said heterologous protein.

2. The method as claimed in claim 1, wherein the liqand responsive element activating sequence is an estrogen responsive element.

3. The method as claimed in claim 1 wherein the receptor is an estrogen receptor, said ligand is an estrogen and the portion of the receptor that recognizes the ligand is obtained from the human estrogen receptor (hER).

4. The method as claimed in claim 3, wherein the ligand responsive element activating sequence is an estrogen responsive element directly repeated two times.

5. The method as claimed in claim 1 wherein the fragment of the receptor that recognizes the ligand is obtained from the human estrogen receptor which has glycine instead of a valine in amino acid position 400 (hERG receptor) as shown in Seq:Id No: 2, the ligand being an estrogen.

6. The method as claimed in claim 5, wherein estradiol is added at a concentration of between 2 nM and 50 nM.

7. The method as claimed in claim 1, wherein, in the yeast, the first DNA fragment encoding said protein under the control of elements providing for expression of said second DNA fragment in yeasts or the DNA fragment encoding said receptor occurs on a plasmid containing an origin of replication functional in yeast.

8. The method as claimed in claim 7, wherein said first DNA fragment and said second DNA fragment occur on the same plasmid.

9. The method as claimed in claim 1, wherein the DNA fragment encoding for the said receptor is carried by a chromosome of the yeast.

10. The method as claimed in claim 1, wherein said yeast is deficient in proteases.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
    (A) LENGTH: 6450 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:1:

```
GAGTTGTGCC TGGAGTGATG TTTAAGCCAA TGTCAGGGCA AGGCAACAGT CCCTGGCCGT      60
CCTCCAGCAC CTTTGTAATG CATATGAGCT CGGGAGACCA GTACTTAAAG TTGGAGGCCC     120
GGGAGCCCAG GAGCTGGCGG AGGGCGTTCG TCCTGGGAGC TGCACTTGCT CCGTCGGGTC     180
GCCGGCTTCA CCGGACCGCA GGCTCCCGGG GCAGGGCCGG GGCCAGAGCT CGCGTGTCGG     240
CGGGACATGC GCTGCGTCGC CTCTAACCTC GGGCTGTGCT CTTTTTCCAG GTGGCCCGCC     300
GGTTTCTGAG CCTTCTGCCC TGCGGGGACA CGGTCTGCAC CCTGCCCGCG GCCACGGACC     360
ATGACCATGA CCCTCCACAC CAAAGCATCT GGGATGGCCC TACTGCATCA GATCCAAGGG     420
AACGAGCTGG AGCCCCTGAA CCGTCCGCAG CTCAAGATCC CCTGGAGCG GCCCCTGGGC      480
GAGGTGTACC TGGACAGCAG CAAGCCCGCC GTGTACAACT ACCCCGAGGG CGCCGCCTAC     540
GAGTTCAACG CCGCGGCCGC CGCCAACGCG CAGGTCTACG GTCAGACCGG CCTCCCCTAC     600
GGCCCCGGGT CTGAGGCTGC GGCGTTCGGC TCCAACGGCC TGGGGGGTTT CCCCCCACTC     660
AACAGCGTGT CTCCGAGCCC GCTGATGCTA CTGCACCCGC CGCCGCAGCT GTCGCCTTTC     720
CTGCAGCCCC ACGCCAGCA GGTGCCCTAC TACCTGGAGA ACGAGCCCAG CGGCTACACG     780
GTGCGCGAGG CCGGCCCGCC GGCATTCTAC AGGCCAAATT CAGATAATCG ACGCCAGGGT     840
GGCAGAGAAA GATTGGCCAG TACCAATGAC AAGGGAAGTA TGGCTATGGA ATCTGCCAAG     900
GAGACTCGCT ACTGTGCAGT GTGCAATGAC TATGCTTCAG GCTACCATTA TGGAGTCTGG     960
TCCTGTGAGG GCTGCAAGGC CTTCTTCAAG AGAAGTATTC AAGGACATAA CGACTATATG    1020
TGTCCAGCCA CCAACCAGTG CACCATTGAT AAAAACAGGA GGAAGAGCTG CCAGGCCTGC    1080
CGGCTCCGCA AATGCTACGA AGTGGGAATG ATGAAAGGTG GGATACGAAA AGACCGAAGA    1140
GGAGGGAGAA TGTTGAAACA CAAGCGCCAG AGAGATGATG GGGAGGGCAG GGGTGAAGTG    1200
GGGTCTGCTG GAGACATGAG AGCTGCCAAC CTTTGGCCAA GCCCGCTCAT GATCAAACGC    1260
TCTAAGAAGA ACAGCCTGGC CTTGTCCCTG ACGGCCGACC AGATGGTCAG TGCCTTGTTG    1320
GATGCTGAGC CCCCCATACT CTATTCCGAG TATGATCCTA CCAGACCCTT CAGTGAAGCT    1380
TCGATGATGG GCTTACTGAC CAACCTGGCA GACAGGGAGC TGGTTCACAT GATCAACTGG    1440
GCGAAGAGGG TGCCAGGCTT TGTGGATTTG ACCCTCCATG ATCAGGTCCA CCTTCTAGAA    1500
TGTGCCTGGC TAGAGATCCT GATGATTGGT CTCGTCTGGC GCTCCATGGA GCACCCAGTG    1560
AAGCTACTGT TTGCTCCTAA CTTGCTCTTG GACAGGAACC AGGGAAAATG TGTAGAGGGC    1620
ATGGTGGAGA TCTTCGACAT GCTGCTGGCT ACATCATCTC GGTTCCGCAT GATGAATCTG    1680
CAGGGAGAGG AGTTTGTGTG CCTCAAATCT ATTATTTTGC TTAATTCTGG AGTGTACACA    1740
TTTCTGTCCA GCACCCTGAA GTCTCTGGAA GAGAAGGACC ATATCCACCG AGTCCTGGAC    1800
AAGATCACAG ACACTTTGAT CCACCTGATG GCCAAGGCAG GCCTGACCCT GCAGCAGCAG    1860
CACCAGCGGC TGGCCCAGCT CCTCCTCATC CTCTCCCACA TCAGGCACAT GAGTAACAAA    1920
GGCATGGAGC ATCTGTACAG CATGAAGTGC AAGAACGTGG TGCCCCTCTA TGACCTGCTG    1980
CTGGAGATGC TGGACGCCCA CCGCCTACAT GCGCCCACTA GCCGTGGAGG GGCATCCGTG    2040
GAGGAGACGG ACCAAAGCCA CTTGGCCACT GCGGGCTCTA CTTCATCGCA TTCCTTGCAA    2100
```

-continued

```
AAGTATTACA TCACGGGGGA GGCAGAGGGT TTCCCTGCCA CAGTCTGAGA GCTCCCTGGC    2160

TCCCACACGG TTCAGATAAT CCCTGCTGCA TTTTACCCTC ATCATGCACC ACTTTAGCCA    2220

AATTCTGTCT CCTGCATACA CTCCGGCATG CATCCAACAC CAATGGCTTT CTAGATGAGT    2280

GGCCATTCAT TTGCTTGCTC AGTTCTTAGT GGCACATCTT CTGTCTTCTG TTGGGAACAG    2340

CCAAAGGGAT TCCAAGGCTA AATCTTTGTA ACAGCTCTCT TTCCCCCTTG CTATGTTACT    2400

AAGCGTGAGG ATTCCCGTAG CTCTTCACAG CTGAACTCAG TCTATGGGTT GGGGCTCAGA    2460

TAACTCTGTG CATTTAAGCT ACTTGTAGAG ACCCAGGCCT GGAGAGTAGA CATTTTGCCT    2520

CTGATAAGCA CTTTTTAAAT GGCTCTAAGA ATAAGCCACA GCAAAGAATT TAAAGTGGCT    2580

CCTTTAATTG GTGACTTGGA GAAAGCTAGG TCAAGGGTTT ATTATAGCAC CCTCTTGTAT    2640

TCCTATGGCA ATGCATCCTT TTATGAAAGT GGTACACCTT AAAGCTTTTA TATGACTGTA    2700

GCAGAGTATC TGGTGATTGT CAATTCACTT CCCCCTATAG GAATACAAGG GGCCACACAG    2760

GGAAGGCAGA TCCCCTAGTT GGCCAAGACT TATTTTAACT TGATACACTG CAGATTCAGA    2820

GTGTCCTGAA GCTCTGCCTC TGGCTTTCCG GTCATGGGTT CCAGTTAATT CATGCCTCCC    2880

ATGGACCTAT GGAGAGCAAC AAGTTGATCT TAGTTAAGTC TCCCTATATG AGGGATAAGT    2940

TCCTGATTTT TGTTTTTATT TTTGTGTTAC AAAAGAAAGC CCTCCCTCCC TGAACTTGCA    3000

GTAAGGTCAG CTTCAGGACC TGTTCCAGTG GGCACTGTAC TTGGATCTTC CCGGCGTGTG    3060

TGTGCCTTAC ACAGGGGTGA ACTGTTCACT GTGGTGATGC ATGATGAGGG TAAATGGTAG    3120

TTGAAAGGAG CAGGGGCCCT GGTGTTGCAT TTAGCCCTGG GGCATGGAGC TGAACAGTAC    3180

TTGTGCAGGA TTGTTGTGGC TACTAGAGAA CAAGAGGGAA AGTAGGGCAG AAACTGGATA    3240

CAGTTCTGAG CACAGCCAGA CTTGCTCAGG TGGCCCTGCA CAGGCTGCAG CTACCTAGGA    3300

ACATTCCTTG CAGACCCCGC ATTGCCTTTG GGGTGCCCT GGGATCCCTG GGTAGTCCA     3360

GCTCTTATTC ATTTCCCAGC GTGGCCCTGG TTGGAAGAAG CAGCTGTCAA GTTGTAGACA    3420

GCTGTGTTCC TACAATTGGC CCAGCACCCT GGGGCACGGG AGAAGGGTGG GGACCGTTGC    3480

TGTCACTACT CAGGCTGACT GGGGCCTGGT CAGATTACGT ATGCCCTTGG TGGTTTAGAG    3540

ATAATCCAAA ATCAGGGTTT GGTTTGGGGA AGAAAATCCT CCCCCTTCCT CCCCCGCCCC    3600

GTTCCCTACC GCCTCCACTC CTGCCAGCTC ATTTCCTTCA ATTTCCTTTG ACCTATAGGC    3660

TAAAAAAGAA AGGCTCATTC CAGCCACAGG GCAGCCTTCC CTGGGCCTTT GCTTCTCTAG    3720

CACAATTATG GGTTACTTCC TTTTTCTTAA CAAAAAAGAA TGTTTGATTT CCTCTGGGTG    3780

ACCTTATTGT CTGTAATTGA AACCCTATTG AGAGGTGATG TCTGTGTTAG CCAATGACCC    3840

AGGTAGCTGC TCGGGCTTCT CTTGGTATGT CTTGTTTGGA AAAGTGGATT TCATTCATTT    3900

CTGATTGTCC AGTTAAGTGA TCACCAAAGG ACTGAGAATC TGGGAGGGCA AAAAAAAAA    3960

AAAAAGTTTT TATGTGCACT TAAATTTGGG GACAATTTTA TGTATCTGTG TTAAGGATAT    4020

GCTTAAGAAC ATAATTCTTT TGTTGCTGTT TGTTTAAGAA GCACCTTAGT TTGTTTAAGA    4080

AGCACCTTAT ATAGTATAAT ATATATTTTT TTGAAATTAC ATTGCTTGTT TATCAGACAA    4140

TTGAATGTAG TAATTCTGTT CTGGATTTAA TTTGACTGGG TTAACATGCA AAAACCAAGG    4200

AAAAATATTT AGTTTTTTTT TTTTTTTTG TATACTTTTC AAGCTACCTT GTCATGTATA    4260

CAGTCATTTA TGCCTAAAGC CTGGTGATTA TTCATTTAAA TGAAGATCAC ATTTCATATC    4320

AACTTTTGTA TCCACAGTAG ACAAAATAGC ACTAATCCAG ATGCCTATTG TTGGATATTG    4380

AATGACAGAC AATCTTATGT AGCAAAGATT ATGCCTGAAA AGGAAAATTA TTCAGGGCAG    4440
```

```
CTAATTTTGC TTTTACCAAA ATATCAGTAG TAATATTTTT GGACAGTAGC TAATGGGTCA      4500

GTGGGTTCTT TTTAATGTTT ATACTTAGAT TTTCTTTTAA AAAAATTAAA ATAAAACAAA      4560

AAAAATTTCT AGGACTAGAC GATGTAATAC CAGCTAAAGC CAAACAATTA TACAGTGGAA      4620

GGTTTTACAT TATTCATCCA ATGTGTTTCT ATTCATGTTA AGATACTACT ACATTTGAAG      4680

TGGGCAGAGA ACATCAGATG ATTGAAATGT TCGCCCAGGG GTCTCCAGCA ACTTTGGAAA      4740

TCTCTTTGTA TTTTTACTTG AAGTGCCACT AATGGACAGC AGATATTTTC TGGCTGATGT      4800

TGGTATTGGG TGTAGGAACA TGATTTAAAA AAAAAACTCT TGCCTCTGCT TTCCCCCACT      4860

CTGAGGCAAG TTAAAATGTA AAAGATGTGA TTTATCTGGG GGGCTCAGGT ATGGTGGGGA      4920

AGTGGATTCA GGAATCTGGG GAATGGCAAA TATATTAAGA AGAGTATTGA AAGTATTTGG      4980

AGGAAAATGG TTAATTCTGG GTGTGCACCA AGGTTCAGTA GAGTCCACTT CTGCCCTGGA      5040

GACCACAAAT CAACTAGCTC CATTTACAGC CATTTCTAAA ATGGCAGCTT CAGTTCTAGA      5100

GAAGAAAGAA CAACATCAGC AGTAAAGTCC ATGGAATAGC TAGTGGTCTG TGTTTCTTTT      5160

CGCCATTGCC TAGCTTGCCG TAATGATTCT ATAATGCCAT CATGCAGCAA TTATGAGAGG      5220

CTAGGTCATC CAAAGAGAAG ACCCTATCAA TGTAGGTTGC AAAATCTAAC CCCTAAGGAA      5280

GTGCAGTCTT TGATTTGATT TCCCTAGTAA CCTTGCAGAT ATGTTTAACC AAGCCATAGC      5340

CCATGCCTTT TGAGGGCTGA ACAAATAAGG GACTTACTGA TAATTTACTT TTGATCACAT      5400

TAAGGTGTTC TCACCTTGAA ATCTTATACA CTGAAATGGC CATTGATTTA GGCCACTGGC      5460

TTAGAGTACT CCTTCCCCTG CATGACACTG ATTACAAATA CTTTCCTATT CATACTTTCC      5520

AATTATGAGA TGGACTGTGG GTACTGGGAG TGATCACTAA CACCATAGTA ATGTCTAATA      5580

TTCACAGGCA GATCTGCTTG GGGAAGCTAG TTATGTGAAA GGCAAATAAA GTCATACAGT      5640

AGCTCAAAAG GCAACCATAA TTCTCTTTGG TGCAAGTCTT GGGAGCGTGA TCTAGATTAC      5700

ACTGCACCAT TCCCAAGTTA ATCCCCTGAA AACTTACTCT CAACTGGAGC AAATGAACTT      5760

TGGTCCCAAA TATCCATCTT TTCAGTAGCG TTAATTATGC TCTGTTTCCA ACTGCATTTC      5820

CTTTCCAATT GAATTAAAGT GTGGCCTCGT TTTTAGTCAT TTAAAATTGT TTTCTAAGTA      5880

ATTGCTGCCT CTATTATGGC ACTTCAATTT TGCACTGTCT TTTGAGATTC AAGAAAAATT      5940

TCTATTCATT TTTTTGCATC CAATTGTGCC TGAACTTTTA AAATATGTAA ATGCTGCCAT      6000

GTTCCAAACC CATCGTCAGT GTGTGTGTTT AGAGCTGTGC ACCCTAGAAA CAACATACTT      6060

GTCCCATGAG CAGGTGCCTG AGACACAGAC CCCTTTGCAT TCACAGAGAG GTCATTGGTT      6120

ATAGAGACTT GAATTAATAA GTGACATTAT GCCAGTTTCT GTTCTCTCAC AGGTGATAAA      6180

CAATGCTTTT TGTGCACTAC ATACTCTTCA GTGTAGAGCT CTTGTTTTAT GGGAAAAGGC      6240

TCAAATGCCA AATTGTGTTT GATGGATTAA TATGCCCTTT TGCCGATGCA TACTATTACT      6300

GATGTGACTC GGTTTTGTCG CAGCTTTGCT TTGTTTAATG AAACACACTT GTAAACCTCT      6360

TTTGCACTTT GAAAAAGAAT CCAGCGGGAT GCTCGAGCAC CTGTAAACAA TTTTCTCAAC      6420

CTATTTGATG TTCAAATAAA GAATTAAACT                                      6450
```

(2) INFORMATION FOR SEQ ID NO:2:

(i) SEQUENCE CHARACTERISTICS:
        (A) LENGTH: 595 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Phe Gly Ser Asn Gly Leu Gly Gly
                85                  90                  95

Phe Pro Pro Leu Asn Ser Val Ser Pro Ser Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415
```

Cys Val Glu Gly Met Val Glu Ile Phe Asp Met Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCGGGTCTAG AAGATCTA                                                        18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CAGATCTTCT AGATTCGA                                                        18

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GATCCAATAT TCCTGGTCAG GCGTGACCGG AGCTGA                36

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTTATAAGGA CCAGTCGCAC TGGCCTCGAC TCTAG                35

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GATCCAATAT TCCCCGTCAG CGTGACCGGA GCTGA                35

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTTATAAGGG GCAGTCGCAC TGGCCTCGAC TCTAG                35

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AAGAAAGACT GGGACTTTGT G                               21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GATTGGATGA AGCCTTACCA C                               21

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
AATTACCGTC GCTCGAGCGA CGGCTCACAG                                    30
```

(2) INFORMATION FOR SEQ ID NO:12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
CGATGTATTT TTCAGACATT TTAAGATCTC CAGCCTGTTT                         40
```

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
GGAGCACCCA GGGAAGCTAC TGT                                           23
```

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
GACACTTCAC ATGAGC                                                   16
```

(2) INFORMATION FOR SEQ ID NO:15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
AGATCTTAAA ATGTCT                                                   16
```